(12) United States Patent
Jung et al.

(10) Patent No.: US 10,219,771 B2
(45) Date of Patent: Mar. 5, 2019

(54) RADIOGRAPHIC IMAGING APPARATUS, METHOD OF CONTROLLING RADIOGRAPHIC IMAGING APPARATUS AND COMPUTED TOMOGRAPHY APPARATUS

(71) Applicant: SAMSUNG ELECTRONICS CO., LTD., Suwon-si (KR)

(72) Inventors: Ji Young Jung, Bucheon-si (KR); Yeong-seon Kim, Wonju-si (KR); Chang Lae Lee, Suwon-si (KR); Jong Hyon Yi, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 591 days.

(21) Appl. No.: 14/794,403

(22) Filed: Jul. 8, 2015

(65) Prior Publication Data

US 2016/0100816 A1 Apr. 14, 2016

(30) Foreign Application Priority Data

Oct. 10, 2014 (KR) ........................ 10-2014-0136660

(51) Int. Cl.
*A61B 6/00* (2006.01)
*A61B 6/03* (2006.01)
(Continued)

(52) U.S. Cl.
CPC .............. *A61B 6/542* (2013.01); *A61B 6/027* (2013.01); *A61B 6/032* (2013.01); *A61B 6/405* (2013.01);
(Continued)

(58) Field of Classification Search
CPC .............. G06F 21/36; G06K 19/06037; H04L 2463/082; H04L 63/08; H04W 12/06;
(Continued)

(56) References Cited

U.S. PATENT DOCUMENTS

| 7,682,078 B2 | 3/2010 | Rietzel |
| 7,945,013 B2 * | 5/2011 | Goto .................... A61B 5/4869 378/16 |

(Continued)

FOREIGN PATENT DOCUMENTS

| JP | 2005143759 A | 6/2005 |
| JP | 2009000225 A | 1/2009 |

(Continued)

OTHER PUBLICATIONS

Communication dated Jun. 28, 2016 issued by Korean Intellectual Property Office in counterpart Korean Patent Application No. 10-2014-0136660.

(Continued)

*Primary Examiner* — Irakli Kiknadze
(74) *Attorney, Agent, or Firm* — Sughrue Mion, PLLC

(57) ABSTRACT

A radiographic imaging apparatus includes: a radiographic image obtainer configured to acquire a first radiographic image of an object; and a processor configured to obtain attenuation information of the object based on the first radiographic image, determine candidate tube voltages and tube currents based on a quality of a second radiographic image to be obtained, and determine expected exposure doses corresponding to the determined candidate tube voltages and tube currents.

27 Claims, 24 Drawing Sheets

(51) Int. Cl.
*A61B 6/02* (2006.01)
*A61B 6/04* (2006.01)

(52) U.S. Cl.
CPC .......... *A61B 6/4233* (2013.01); *A61B 6/4464* (2013.01); *A61B 6/488* (2013.01); *A61B 6/50* (2013.01); *A61B 6/5205* (2013.01); *A61B 6/544* (2013.01); *A61B 6/545* (2013.01); *A61B 6/0407* (2013.01)

(58) Field of Classification Search
CPC ....... A61B 6/027; A61B 6/032; A61B 6/0407; A61B 6/405; A61B 6/4233; A61B 6/4464; A61B 6/488; A61B 6/50; A61B 6/5205; A61B 6/542; A61B 6/544; A61B 6/545; A61B 6/461; A61B 6/10; A61B 6/4078; A61B 6/482; A61B 6/583; A61B 5/4869; A61B 6/4035; A61B 6/4241; A61B 6/4441; A61B 6/467; A61B 6/503; A61B 6/505; A61B 6/5252; A61B 6/5282; A61B 6/5294; A61B 6/4085; A61B 6/5258; A61B 6/463; A61B 6/481; A61B 6/466; A61B 6/56; A61B 5/0456; A61B 6/035; A61B 6/06; A61B 6/4021; A61B 6/469; A61B 6/504; G06T 11/005; G01N 2223/419; G01N 2223/612; G01N 23/046; H05H 13/02; H05H 7/04; H05H 2007/004; H05H 7/10; H05H 2007/043; H05H 13/005; H05H 13/04; H05H 2007/046; H05H 7/12; H05H 2007/002; H05H 2007/048; H05H 2007/082; H05H 2007/122; H05H 2277/11; H05H 7/02; A61N 5/1077; A61N 2005/1087; A61N 2005/1095; A61N 5/1048; A61N 5/1081

USPC ...................................... 378/4, 16, 18, 19, 62
See application file for complete search history.

(56) References Cited

U.S. PATENT DOCUMENTS

| | | | |
|---|---|---|---|
| 8,744,039 B2* | 6/2014 | Hirokawa | A61B 6/032 378/108 |
| 2008/0089464 A1 | 4/2008 | Rietzel | |
| 2009/0168950 A1 | 7/2009 | Jianying | |
| 2015/0201899 A1* | 7/2015 | Uchinomiya | A61B 6/4405 378/62 |
| 2015/0378030 A1* | 12/2015 | Tamura | G01N 23/04 378/98.2 |
| 2017/0055935 A1* | 3/2017 | Takahashi | A61B 5/055 |

FOREIGN PATENT DOCUMENTS

| | | |
|---|---|---|
| JP | 4545404 B2 | 9/2010 |
| JP | 2011212434 A | 10/2011 |

OTHER PUBLICATIONS

Communication dated Jan. 19, 2017, issued by the Korean Intellectual Property Office in counterpart Korean application No. 10-2014-0136660.

Communication dated Mar. 18, 2017, issued by the Korean Intellectual Property Office in counterpart Korean application No. 10-2014-0136660.

Cynthia H. McCollough; "The Latest in Radiation Dose Reduction Techniques in CT"; 2010; Mayo Clinic; http://mayoresearch.mayo.edu/CTCIC; 70 pgs.

Communication dated Jul. 20, 2015, issued by the International Searching Authority in counterpart International Application No. PCT/KR2015/005759 (PCT/ISA/210).

\* cited by examiner

FIG. 12

| SET # | TUBE VOLTAGE | TUBE CURRENT |
|---|---|---|
| 1 | 80 | 180 |
| 2 | 100 | 85 |
| 3 | 120 | 50 |
| 4 | 140 | 30 |
| ⋮ | ⋮ | ⋮ |

FIG. 14

| TUBE VOLTAGE | TUBE CURRENT | EXPECTED EXPOSURE DOSE |
|---|---|---|
| 80 | 180 | 3 |
| 100 | 85 | 2 |
| 120 | 50 | 4 |
| 140 | 30 | 5 |

RADIOGRAPHIC IMAGING APPARATUS, METHOD OF CONTROLLING RADIOGRAPHIC IMAGING APPARATUS AND COMPUTED TOMOGRAPHY APPARATUS

CROSS-REFERENCE TO RELATED APPLICATION

This application claims priority from Korean Patent Application No. 10-2014-0136660, filed on Oct. 10, 2014 in the Korean Intellectual Property Office, the disclosure of which is incorporated herein by reference in its entirety.

BACKGROUND

1. Field

Apparatuses and methods consistent with exemplary embodiments relate to a radiographic imaging apparatus, a method of controlling the radiographic imaging apparatus, and a computed tomography (CT) apparatus.

2. Description of the Related Art

Radiographic imaging apparatuses capture an image of an object using properties of radiographic rays in which the radiographic rays, such as X-rays, are absorbed by the object or transmitted through the object according to characteristics of the object material. The radiographic imaging apparatuses receive the radiographic rays transmitted through the object or generated in the object and generate a radiographic image according to the received radiographic rays, thereby providing an image of internal areas of the object. Since the structure of the inside of the object can be easily understood using the radiographic imaging apparatuses, the radiographic imaging apparatuses have been used in various industrial fields. For example, the radiographic imaging apparatuses are used to detect lesions in the human body in a hospital and so on, or to understand an internal structure of an object or a part in a factory and so on. Also, the radiographic imaging apparatuses are used to check luggage in an airport security zone and so on. Examples of the radiographic imaging apparatuses include digital radiography (DR) apparatuses, CT apparatuses, and full field digital mammography (FFDM) apparatuses.

SUMMARY

One or more exemplary embodiments provide a radiographic imaging apparatus that is capable of obtaining a user's desired radiographic image while minimizing an exposure dose of an object according to the user's desired image quality, a method of controlling the radiographic imaging apparatus, and a CT apparatus.

One or more exemplary embodiments provide a radiographic imaging apparatus that is capable of determining a tube voltage that is capable of obtaining an image with good quality while minimizing an exposure dose of the object without information regarding the size or characteristics of the object, a method of controlling the radiographic imaging apparatus, and a CT apparatus.

In accordance with an aspect of an exemplary embodiment, a radiographic imaging apparatus includes: a radiographic image obtainer configured to capture a radiographic image of an object; and a processor configured to obtain attenuation information of the object based on the radiographic image obtained by irradiating the object with radiographic rays, determine at least one tube voltage and tube current based on quality of a radiographic image to be obtained, and determine at least one expected exposure dose corresponding to each of the at least one tube voltage and tube current.

The processor may select a tube voltage and a tube current that correspond to a smallest expected exposure dose and may recommend the selected tube voltage and tube current to a user.

The processor may determine an equivalent corresponding to the object based on the attenuation information of the object and may determine the at least one tube voltage and tube current further using the determined equivalent.

The processor may determine an equivalent corresponding to the object based on the attenuation information of the object by referring to first data regarding the relationship between a tube voltage of the radiographic rays, attenuation information, and an equivalent.

The equivalent may include a water equivalent object (WEO).

The processor may determine at least one tube voltage and tube current using second data regarding the relationship between a tube voltage, an equivalent, and a tube current.

The processor may determine at least one expected exposure dose corresponding to each of the at least one tube voltage and tube current using third data regarding the relationship between a tube voltage, a tube current, and an expected exposure dose.

The radiographic imaging apparatus may further include an input unit to which quality of the radiographic image to be obtained is input from the user.

The processor may determine a plurality of equivalents corresponding to a plurality of parts of the object in each of the plurality of parts of the object.

The processor may determine a plurality of tube voltages and tube currents based on quality of an image set in each of the plurality of equivalents corresponding to the plurality of parts of the object and the plurality of equivalents and may determine a plurality of expected exposure doses corresponding to the plurality of obtained tube voltages and tube currents based on the plurality of equivalents.

The processor may select a tube voltage and a tube current corresponding to a smallest expected exposure dose of the plurality of obtained expected exposure doses and may control the radiographic rays corresponding to the tube voltage to irradiate an entire object with the radiographic rays.

The processor may control the radiographic rays corresponding to the tube voltage and the tube current corresponding to the plurality of parts of the object to irradiate the plurality of parts of the object with the radiographic rays.

In accordance with an aspect of an exemplary embodiment, a method of controlling a radiographic imaging apparatus includes: obtaining a radiographic image of an object by irradiating the object with radiographic rays; obtaining attenuation information of the object based on the radiographic image and determining at least one tube voltage and tube current based on set quality of an image; and determining at least one expected exposure dose corresponding to each of the obtained at least one tube voltage and tube current.

The method may further include selecting a tube voltage and a tube current that correspond to a smallest expected exposure dose and recommending the selected tube voltage and tube current to a user.

The determining of the tube voltage and the tube current may include determining attenuation information of the object using the radiographic image and determining an equivalent corresponding to the object based on the attenuation information of the object.

The determining of the equivalent corresponding to the object based on the attenuation information of the object may include determining an equivalent corresponding to the object based on the attenuation information of the object by referring to first data regarding the relationship between a tube voltage of the radiographic rays, attenuation information, and an equivalent.

The equivalent may include a water equivalent object (WEO).

The determining of the at least one tube voltage and tube current may include determining at least one tube voltage and tube current using second data regarding the relationship between a tube voltage, an equivalent, and a tube current.

The determining of the at least one expected exposure dose may include determining at least one expected exposure dose corresponding to each of the at least one tube voltage and tube current using third data regarding the relationship between a tube voltage, a tube current, and an expected exposure dose.

The method may further include receiving quality of an image from a user.

The method may further include determining a plurality of equivalents corresponding to a plurality of parts of the object in each of the plurality of parts of the object.

The determining of the at least one tube voltage and tube current may include determining a plurality of tube voltages and tube currents based on quality of an image set in each of the plurality of equivalents corresponding to the plurality of parts of the object and the plurality of equivalents, and the determining of the at least one expected exposure dose may include determining a plurality of expected exposure doses corresponding to the plurality of obtained tube voltages and tube currents based on the plurality of equivalents.

The method may further include selecting a tube voltage and a tube current corresponding to a smallest expected exposure dose of the plurality of obtained expected exposure doses and irradiating an entire object with the radiographic rays corresponding to the tube voltage.

The irradiating of the radiographic rays may include irradiating the plurality of parts of the object with the radiographic rays corresponding to the tube voltage and the tube current corresponding to the plurality of parts of the object.

In accordance with an aspect of an exemplary embodiment, a CT apparatus includes: a gantry; a radiographic radiation source installed in the gantry, configured to irradiate an object with radiographic rays and to be rotatable; a radiographic detector installed in the gantry, configured to receive the radiographic rays transmitting the object and output electrical signals corresponding to the received radiographic rays; an image processor configured to obtain a radiographic image based on the output electrical signals; and a processor configured to obtain attenuation information of the object based on the radiographic image obtained by irradiating the object with radiographic rays, determine at least one tube voltage and tube current based on quality of a radiographic image to be obtained and determine at least one expected exposure dose corresponding to each of the at least one tube voltage and tube current.

The processor may select a tube voltage and a tube current that correspond to a smallest expected exposure dose and may recommend the selected tube voltage and tube current to a user.

The processor may determine an equivalent corresponding to the object based on the attenuation information of the object and may determine the at least one tube voltage and tube current further using the determined equivalent.

BRIEF DESCRIPTION OF THE DRAWINGS

The above aspects and/or other aspects will become more apparent by describing certain exemplary embodiments with reference to the accompanying drawings, in which:

FIG. 12 is a view of the obtained tube voltage and tube current according to an exemplary embodiment;

FIG. 14 is a view of an operation of selecting a third lookup table and a smallest exposure dose of expected exposure doses;

DETAILED DESCRIPTION

Figure 1:
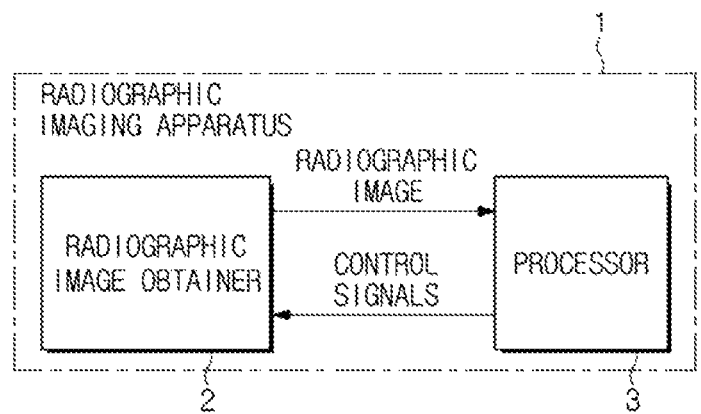
FIG. 1 is a view of a configuration of a radiographic imaging apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions are not described in detail since they would obscure the description with unnecessary detail.

The thicknesses of lines or sizes of elements shown in the drawings while the radiographic imaging apparatus, the method of controlling the radiographic imaging apparatus, and the CT apparatus are described, may be exaggerated for clarity and convenience of explanation.

FIG. 1 is a view of a configuration of a radiographic imaging apparatus according to an exemplary embodiment. As illustrated in FIG. 1, a radiographic imaging apparatus 1 may include a radiographic image obtainer 2 that obtains a radiographic image of an object and a processor 3 that controls an operation of the radiographic image obtainer 2.

The radiographic imaging apparatus 1 may include various radiographic devices that capture an image of the object using radiographic rays. For example, the radiographic imaging apparatus 1 may be a DR apparatus, an FFDM apparatus, or a CT apparatus. The radiographic imaging apparatus 1 may further include an apparatus that is capable of obtaining an image of the object using the radiographic rays. The radiographic imaging apparatus 1 may represent one physical entity that is capable of obtaining the radiographic image or a combination of a plurality of entities that are capable of obtaining the radiographic image while being connected to each other via a wired and/or wireless communication network and operating respectively.

The object may be a living thing, such as a human or an animal, or a nonliving thing, such as a part or a luggage. Also, the object may be a phantom. The object may be the entirety or a part of a particular article. For example, the object may be a particular part or a portion of the human body, for example, four limbs or an organ.

The radiographic image obtainer 2 may obtain the radiographic image of the object using the radiographic rays. The radiographic image obtainer 2 may irradiate the object with the radiographic rays, receive the radiographic rays transmitting the object, convert the received radiographic rays into electrical signals, and obtain the radiographic image based on the electrical signals. The radiographic image may be raw data. The radiographic image obtainer 2 may include a radiation source and a detector to obtain the radiographic image. The radiation source may include a radiographic tube. The radiographic tube may be controlled by a tube current and a tube voltage applied to the radiographic tube. The radiographic image obtained by the radiographic image obtainer 2 may be transmitted to the processor 3.

The processor 3 may generate control signals used to control an operation of the radiographic image obtainer 2 based on the radiographic image transmitted from the radiographic image obtainer 2 and then may transmit the generated control signals to the radiographic image obtainer 2. The processor 3 may be implemented by one or more semiconductor chips disposed in the radiographic imaging apparatus 1 and/or by one or more semiconductor chips disposed on a workstation implemented with a computer outside the radiographic imaging apparatus 1.

FIG. 1 illustrates an exemplary embodiment in which the processor 3 generates the control signals based on the radiographic image transmitted from the radiographic image obtainer 2 of the radiographic imaging apparatus 1. However, a radiographic image for generating the control signals is not limited to the radiographic image generated by the radiographic image obtainer 2, and the processor 3 may generate the control signals used to control the radiographic image obtainer 2 by receiving the radiographic image obtained by an imaging apparatus different from the radiographic imaging apparatus 1. An imaging apparatus different from the radiographic imaging apparatus 1 may be the same type of imaging apparatus or a different type of imaging apparatus, as for example, a positron emission tomography (PET) apparatus, a single photon emission computed tomography (SPECT) apparatus, the DR apparatus, the FFDM apparatus, and/or the CT apparatus.

The processor 3 may determine an equivalent corresponding to the object imaged by the radiographic image obtainer 2. The equivalent may include a water-equivalent object (WEO) or a water equivalent phantom. The WEO may refer to an actual or virtual object including water having the same characteristics as predetermined characteristics of the object. Here, the characteristics may include an attenuation rate. The processor 3 may determine the equivalent by referring to previous data obtained theoretically or empirically. The tube voltage used to radiate the radiographic rays in the radiographic image obtainer 2 and the attenuation rate of the object may be used to determine the equivalent. The equivalent may also be determined in each particular zone of the radiographic image.

The processor 3 may obtain at least one tube voltage and tube current based on set image quality and the determined equivalent. The processor 3 may obtain at least one tube voltage and tube current by referring to the previous data obtained theoretically or empirically. The processor 3 may also obtain at least one tube voltage and tube current according to the quality of the radiographic image to be obtained.

The processor 3 may determine an expected exposure dose corresponding to the obtained tube voltage and/or tube current and may control the radiographic image obtainer 2 according to the expected exposure dose. The processor 3 may determine the expected exposure dose using the previous data obtained in advance.

After the expected exposure dose is determined, the processor 3 may control the radiographic image obtainer 2 to select the tube voltage and the tube current, of which expected exposure dose is minimal, from combinations of tube voltages and tube currents and to apply the selected tube voltage and tube current to the radiographic tube. The radiographic image obtainer 2 may obtain the radiographic image by irradiating the object with the radiographic rays according to the tube voltage and tube current selected by the processor 3, by minimizing the exposure dose of the object.

The CT apparatus as an example of the radiographic imaging apparatus which is described in detail below with reference to FIGS. 2 through 18.

Figure 2:
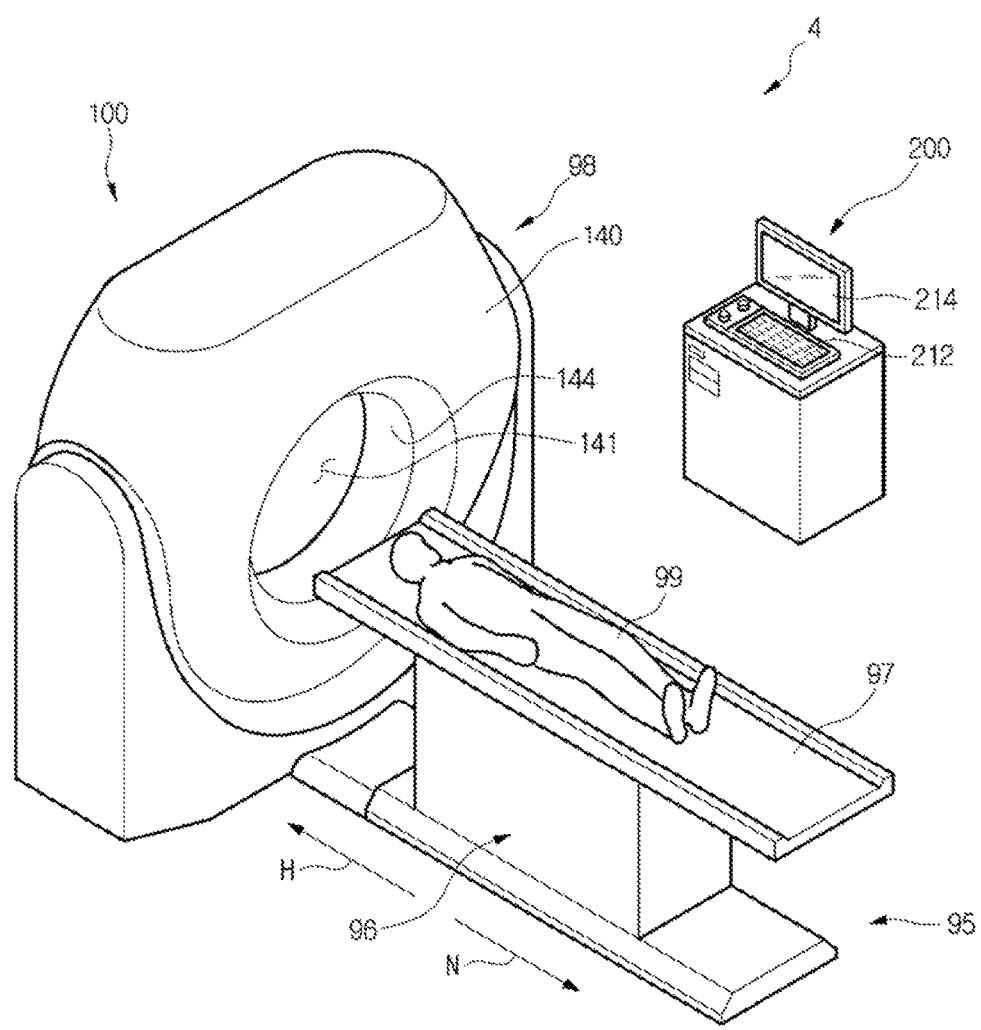
FIG. 2 is a perspective view of a CT apparatus according to an exemplary embodiment.
Figure 3:
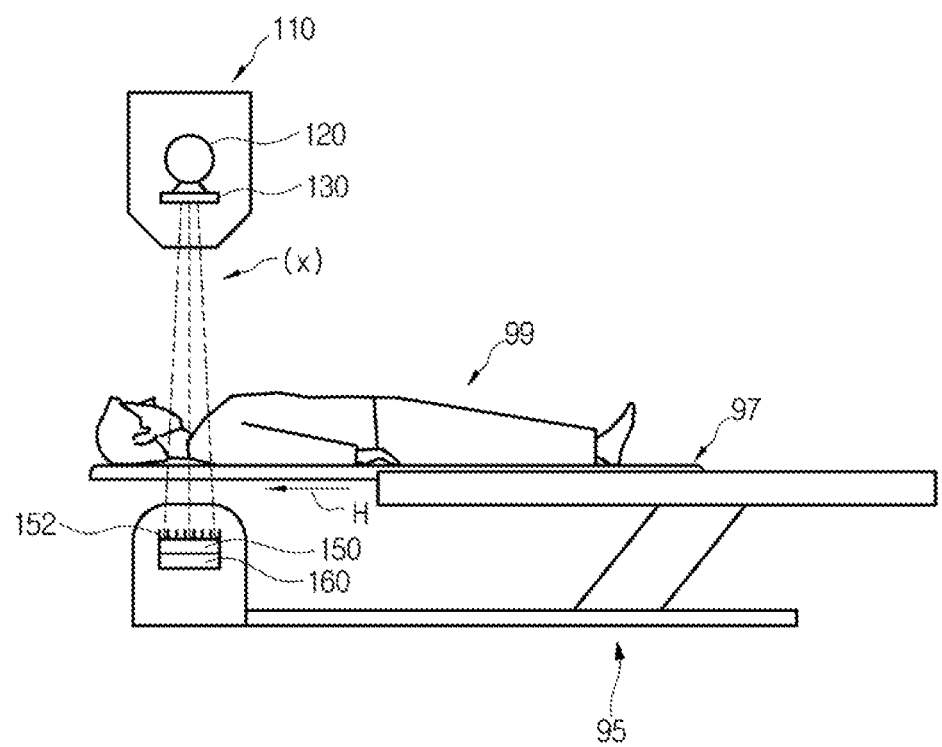
FIG. 3 is a view of the CT apparatus according to an exemplary embodiment.
Figure 4:
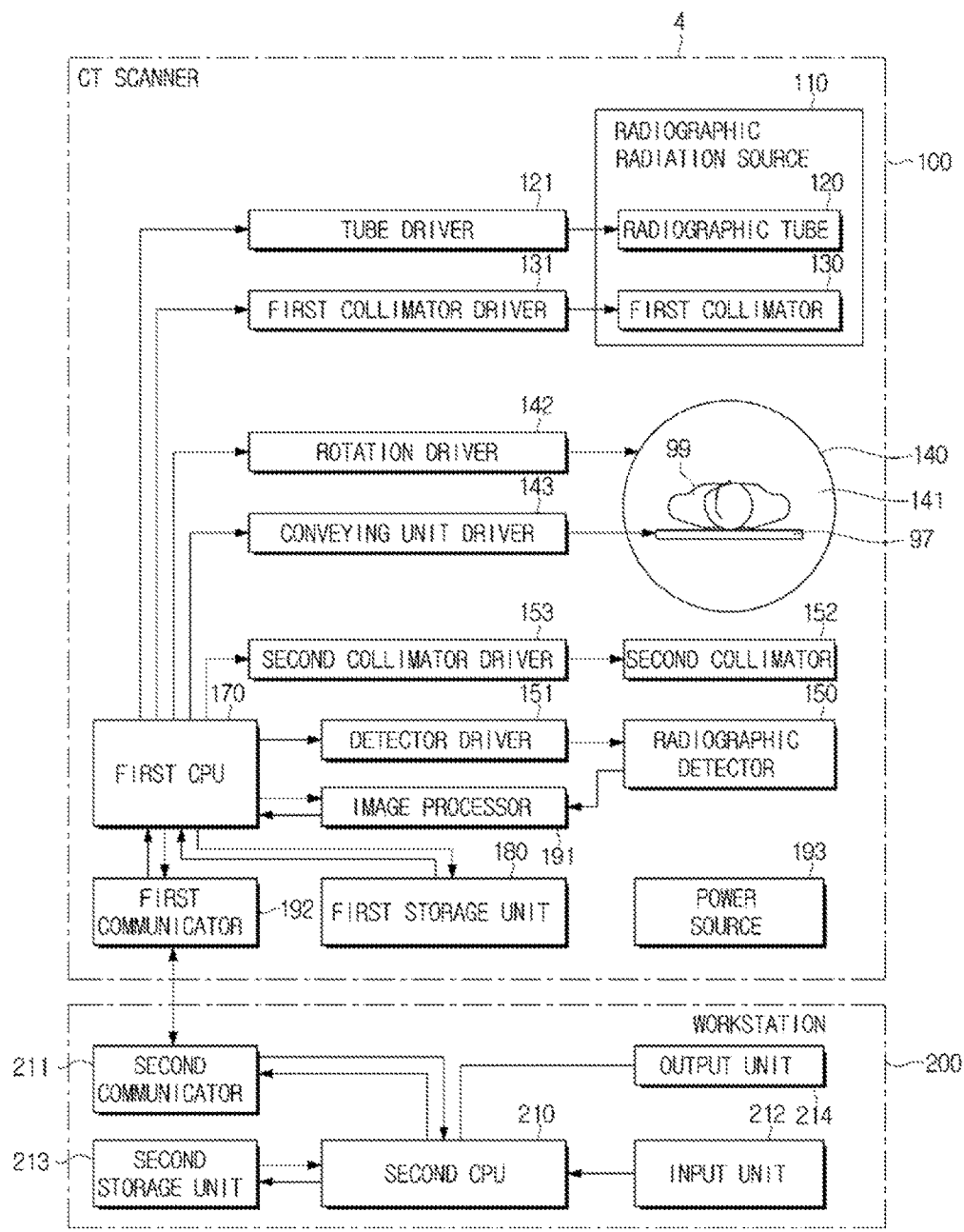
FIG. 4 is a view of the CT apparatus according to an exemplary embodiment.

Referring to FIGS. 2 through 4, a CT apparatus 4 may include an image obtainer, for example, a CT scanner 100 that captures an image of the object, and a workstation 200 for controlling the CT scanner 100. The CT scanner 100 and the workstation 200 may be connected to each other via a wired communication network and/or a wireless communication network.

As illustrated in FIGS. 2 and 3, the CT scanner 100 may include an external housing 98 in which various parts of the CT scanner 100 are embedded. The external housing 98 may include a gantry 140. Various parts for radiographic imaging may be installed in the gantry 140. For example, a radiographic radiation source 110 and a radiographic detector 150 may be installed in the gantry 140. The radiographic radiation source 110 and the radiographic detector 150 may be rotated together inside the gantry 140. A bore 141 having a circular, oval, triangular, or rectangular shape may be formed in a portion of the gantry 140, for example, in the center of the gantry 140. The radiographic radiation source 110 and the radiographic detector 150 may perform radiographic irradiation and receive radiographic rays, respectively, while being rotated or moved along an outer surface 144 of the bore 141.

The radiographic radiation source 110 may include a radiographic tube 120 that generates and radiates the radiographic rays and a first collimator 130 that guides the irradiated radiographic rays.

The CT scanner 100 may include a conveying unit 95 for conveying an object 99 into the bore 141. The conveying unit 95 may include a table 97 on which the object 99 is placed, and a support 96 that supports the table 97. The table 97 may be moved at a predetermined speed inside the bore 141 in a first direction H due to an operation of a conveying unit driver 143, such as a motor or an actuator. The predetermined speed may be fixed or variable. The conveying unit driver 143 may be disposed in the support 96. A wheel or rail may be disposed in the table 97 or support 96 so that the table 97 may be moved according to the operation of the conveying unit driver 143. As the table 97 is moved, the object 99 on the table 97 is conveyed into the bore 141. After imaging is finished, the table 97 may be moved in an opposite second direction N and may convey the object 99 to an outside of the bore 141.

Referring to FIGS. 3 and 4, the CT scanner 100 may further include a second collimator 152, tube driver 121, first collimator driver 131, rotation driver 142, detector driver 151, and second collimator driver 153, a first CPU 170, a first storage unit 180, an image processor 191, a first communicator 192, and a power source 193. However, one or more of the above-described elements of the CT scanner 100 may be omitted or disposed in the workstation 200 according to an exemplary embodiment.

Figure 5:
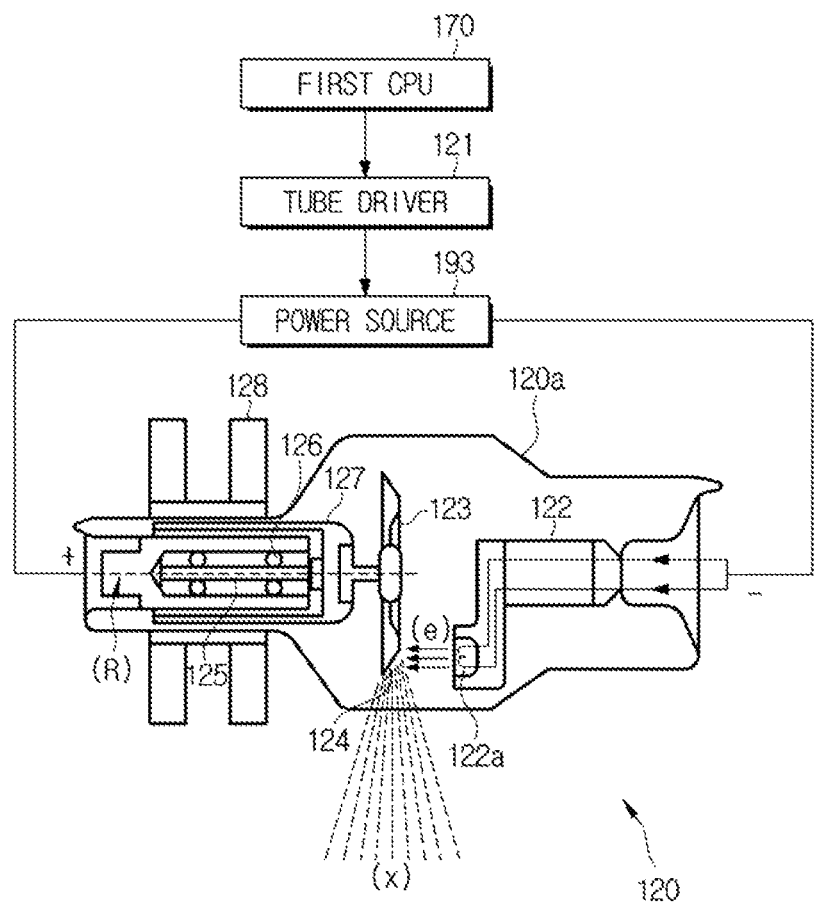
FIG. 5 is a view of a radiographic tube according to an exemplary embodiment.

FIG. 5 is a view of a radiographic tube according to an exemplary embodiment of the present invention. Referring to FIG. 5, the radiographic tube 120 may be electrically connected to the power source 193 or to an external power source (not shown). The power source 193 may apply predetermined voltage and current to the radiographic tube 120 according to control of a CPU 190 and the tube driver 121. If the predetermined voltage and current are applied to the radiographic tube 120, the radiographic tube 120 may generate radiographic rays having a uniform size according to the applied predetermined voltage and current. A potential difference between a cathode filament 122a and an anode 123 of the radiographic tube 120 is referred to as a tube potential, and a current flowing due to electrons that collide with the anode 123 is referred to as a tube current. If the tube voltage is increased, the speed of the electrons is increased. Thus, the size of generated energy of the radiographic rays is increased. If the tube current is increased, a radiation dose of the radiographic rays may be increased. Thus, by adjusting the voltage and the current applied by the power source 193, an energy spectrum and a radiation dose of the irradiated radiographic rays may be adjusted.

Referring to FIG. 5, the radiographic tube 120 may include a tubular body 120a, a cathode 122, and the anode 123. The tubular body 120a may support various parts used to generate the radiographic rays, such as the cathode 122 and the anode 123, while these parts are embedded in the tubular body 120a. The tubular body 120a may be shielded so that the electrons that are generated in the cathode 122 and move to the anode 123, are not be exposed to the outside. A degree of vacuum inside the tubular body 120a may be maintained relatively high, at about $10^{-7}$ mmHg. The tubular body 120a may be a glass tube formed of predetermined silicic acid hard glass. Electron beams e may be radiated from the cathode 122 toward the anode 123. The filament 122a onto which the electrons are gathered, may be disposed on a distal end of the cathode 122. The filament 122a may be heated according to the applied tube voltage and may emit the electrons collected on the filament 122a to an inside of the tubular body 120a. The electron beams e emitted from the filament 122a may be accelerated in the tubular body 120a and may move in the direction of the anode 123. Energy of the electron beams e emitted to the inside of the tubular body 120a may be determined according to the tube voltage. The filament 122a of the cathode 122 may be manufactured of a metal, such as tungsten W. According to an exemplary embodiment, carbon nanotubes may be provided, instead of the filament 122a. Predetermined radiographic rays may be generated in the anode 123. A target surface 124 on which the electrons e collide with the anode 123, may be formed on the anode 123. Radiographic rays x of energy corresponding to the applied tube voltage are generated on the target surface 124 as the electrons e are rapidly decelerated. Since the target surface 124 is cut in a predetermined direction, as illustrated in FIG. 5, the generated radiographic rays x may be mainly radiated in a predetermined direction. The anode 123 may be formed of a metal, such as copper (Cu), and the target surface 124 may be formed of a metal, such as W, chrome (Cr), iron (Fe), or nickel (Ni).

According to an exemplary embodiment, as illustrated in FIG. 5, the anode 123 may be a rotation anode having a disc shape. A distal end of the rotation anode 123 may be cut at a predetermined angle, and the target surface 124 may be formed in the cut part of the distal end of the rotation anode 123. The rotation anode 123 may rotate about a predetermined axis R at predetermined speed. For rotation of the rotation anode 123, a stator 128 that generates a rotation magnetic field, a rotor 127 that rotates according to the rotation magnetic field generated by the stator 128 and rotates the rotation anode 123, a bearing 126 that rotates according to rotation of the rotor 127, and an axial member 125 that is the rotation axis R of the rotation anode 123, may be disposed on the radiographic tube 120. The rotor 127 may be a permanent magnet. A focus size of the rotation anode 123 may be reduced compared to a fixed anode while a heat accumulation rate of the rotation anode 123 is increased. Thus, a clearer radiographic image may be obtained. According to another embodiment, the anode 123 may be a fixed anode having a cylindrical shape in which a surface onto which the electron beams are radiated, is cut at a predetermined cutting angle. The target surface 124 may be formed in the cut portion of the fixed anode. According to an exemplary embodiment, the radiographic radiation source 110 may also include a plurality of radiographic tubes 120.

The first collimator 130 may filter a plurality of radiographic rays radiated from the radiographic tube 120 and may guide the radiographic rays to irradiate a predetermined zone with the radiographic rays in a particular direction. The first collimator 130 may include an opening through which the radiographic rays radiated in the particular direction pass, and collimator blades that absorb the radiographic rays radiated in a different direction. A user may control an irradiation direction of the radiographic rays and an irradiation range of the radiographic rays using the position or size of the opening of the first collimator 130. The collimator blades of the first collimator 130 may be formed of a material that may absorb the radiographic rays, such as lead (Pb).

Figure 6:
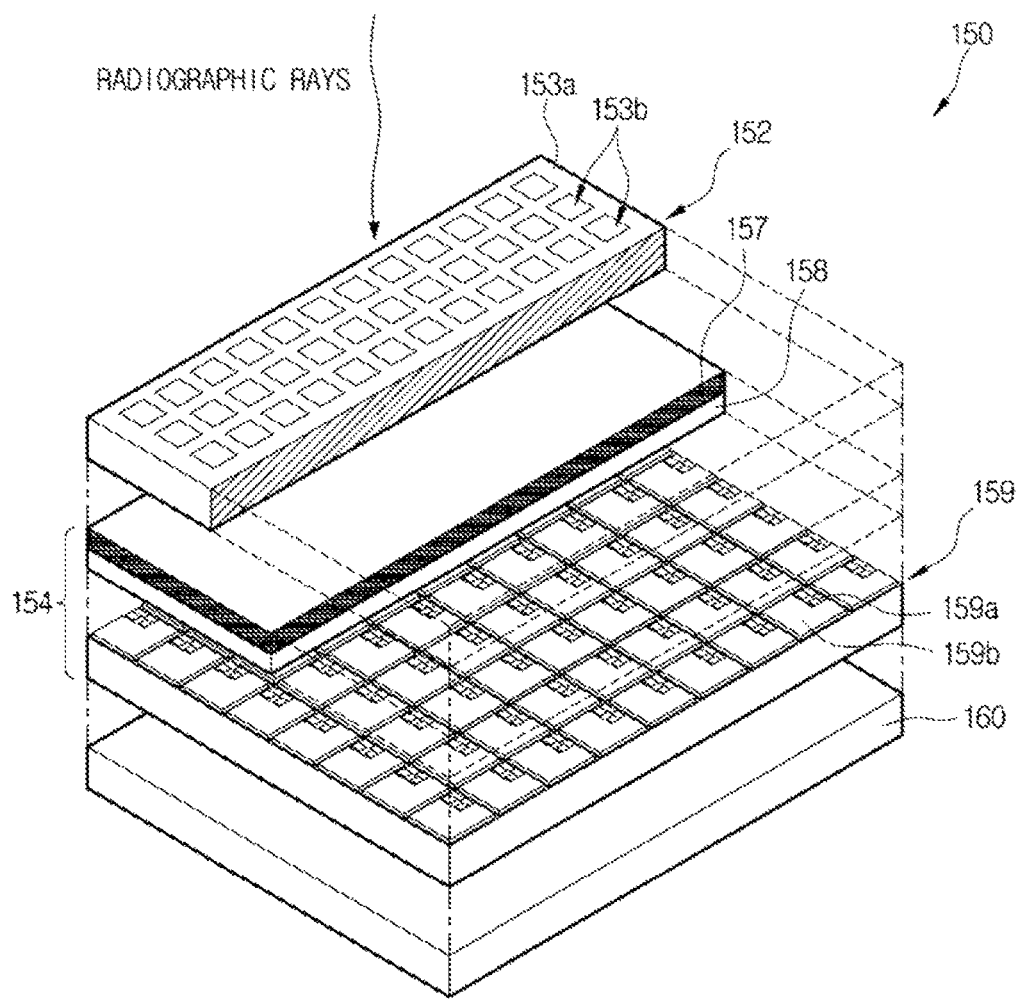
FIG. 6 is a view of a radiographic detector according to an exemplary embodiment.

FIG. 6 is a view of a radiographic detector according to an exemplary embodiment. The object 99 inside the bore 141 may be irradiated with the radiographic rays x radiated by the radiographic radiation source 110. The radiographic rays transmitted through the object 99 may pass through the second collimator 152 and then may reach the radiographic detector 150.

The second collimator 152 may absorb the radiographic rays scattered while passing through the inside of the object 99 and may cause only the radiographic rays in an appropriate direction to reach a detection panel 154 of the radiographic detector 150. The second collimator 152 may include a plurality of barrier walls 153*a* that block the radiographic rays, and transmission openings 153*b* through which the radiographic rays pass. The plurality of barrier walls 153*a* may be formed of a material, such as Pb, and thus may absorb the scattered or refracted radiographic rays, and the transmission openings 153*b* may allow unscattered or unrefracted radiographic rays to pass through.

The radiographic detector 150 may receive the radiographic rays, may convert the received radiographic rays into corresponding electrical signals, and may output the electrical signals. According to an exemplary embodiment, the radiographic detector 150 may directly convert the radiographic rays into the electrical signals (direct method) or may generate visible rays according to the radiographic rays and then may convert the visible rays into the electrical signals (indirect method). When the radiographic detector 150 converts the radiographic rays into the electrical signals using the direct method, the radiographic detector 150 may include a first electrode 157 having one surface on which the radiographic rays are incident, a semiconductor material layer 158 installed on the other surface of the first electrode 157 on which the radiographic rays are not incident, a detection panel 154 including a flat panel 159 installed on the semiconductor material layer 158, and a substrate 160 installed at a rear side of the detection panel 154. Here, a second electrode (pixel electrode) 159*a* and a thin film transistor 159*b* that are to be arranged in one or more rows, may be installed on the flat panel 159 installed on the semiconductor material layer 158. The first electrode 157 may be an electrode having a positive (+) or negative (−) polarity, and the second electrode 159*a* may have an opposite polarity to that of the first electrode 157. A predetermined bias voltage may be applied between the first electrode 157 and the second electrode 159*a*. The semiconductor material layer 158 generates predetermined charge-hole pairs according to incidence and absorption of the radiographic rays. The generated charge-hole pairs may be move toward the first electrode 157 or the second electrode 159*a* according to the polarity of the first electrode 157 or the second electrode 159*a*. The second electrode 159*a* may receive holes or negative charges transmitted from the semiconductor material layer 158 and may output the electrical signals. The thin film transistor 159*b* may read the electrical signals transmitted from the corresponding second electrode 159*a*. The second electrode 159*a* and the thin film transistor 159*b* that correspond to each other, may be installed in one complementary metal-oxide semiconductor (CMOS) chip. When the radiographic detector 150 converts the radiographic rays into the electrical signals using the indirect method, a phosphor screen that outputs visible rays corresponding to the received radiographic rays, may be disposed between the second collimator 152 and the radiographic detection panel 154, and a photodiode, instead of the second electrode 159*a* may be installed on the flat panel 159 to convert the visible rays into the electrical signals. The radiographic detection panel 154 may include a scintillator that outputs visible photons according to the radiographic rays, and a photodiode that detects the visible photons. The radiographic detector 150 may be a photon counting detector (PCD) according to an exemplary embodiment. The substrate 160 may be attached to a rear side of the radiographic detection panel 150, may control various operations of the radiographic detection panel 150, or may store the electrical signals output from the radiographic detection panel 154.

The electrical signals obtained by the radiographic detector 150 may be transmitted to the image processor 191. The image processor 191 may generate an image having a shape in which the user can easily understand the internal structure of the object 99 based on the obtained electrical signals, and may perform additional image processing as needed. The image processor 191 may include a graphics processing unit (GPU). The GPU may include a semiconductor chip, such as a graphic chip. Various operations or functions of the image processor 191 may also be performed by the first CPU 170 or a second CPU 210 of the workstation 200. The image processor 191 may be omitted. The generated radiographic image may be transmitted to the first CPU 170, the first storage unit 180, and/or the workstation 200 through the first communicator 192 and a second communicator 211.

Figure 7:
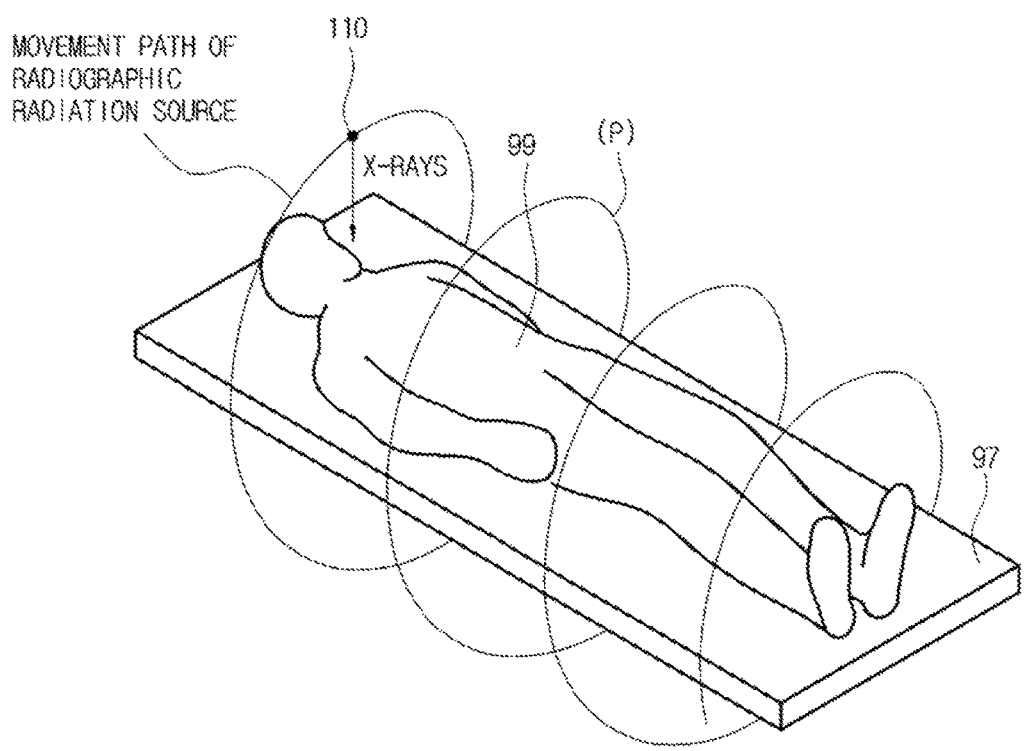
FIG. 7 is a view of radiographic imaging.

With reference to FIG. 7, the radiographic radiation source 110 and the radiographic detector 150 may repeatedly capture a radiographic image of the object 99 while being rotated. As the object 99 is moved to the bore 141, the radiographic radiation source 110 and the radiographic detector 150 facilitate capturing the radiographic image of the object 99 while rotating and moving along a spiral trajectory p around the object 99. Thus, the radiographic radiation source 110 and the radiographic detector 150 may facilitate capturing a tomography image of the entire object 99.

The first CPU 170 may control various components of the CT scanner 100. The first CPU 170 may generate control instructions according to previously-stored settings or the user's selection and then may transmit the generated control instructions to the radiographic radiation source 110, the second collimator 150, the radiographic detector 150, the image processor 191, the gantry 140, or the conveying unit driver 143 and may control an operation of the CT scanner 100, such as radiographic imaging and image processing. The first CPU 170 may transmit the control instructions to one or all of the tube driver 121, first collimator driver 131, rotation driver 142, conveying unit driver 143, detector driver 151, and second collimator driver 153 and may control an operation of each part. The first CPU 170 may transmit the control signals to the tube driver 121, first collimator driver 131, rotation driver 142, conveying unit driver 143, detector driver 151, and second collimator driver 153 at a certain time so that each part may operate. However, all or one of the tube driver 121, first collimator driver 131, rotation driver 142, conveying unit driver 143, detector driver 151, and second collimator driver 153 may be omitted according to an exemplary embodiment. The first CPU 170 may perform an arithmetic operation or processing function and may be implemented by one or more semiconductor chips disposed on a printed circuit board (PCB).

The tube driver 121 may cause a predetermined tube voltage and tube current to be applied to the radiographic tube 120 by turning on/off a switch connected to the radiographic tube 120 according to the control instructions of the first CPU 170. The first collimator driver 131 may operate the first collimator 130 by expanding or reducing the opening of the first collimator 130 according to the control instructions of the first CPU 170. The rotation driver 142 may rotate the radiographic radiation source 110, the first collimator 130, the second collimator 152, and the radiographic detector 150 according to the control instructions of the first CPU 170. The conveying unit driver 143 may operate according to the control instructions of the first CPU 170 and may move the table 97 in the first direction H of the bore 141 of the external housing 98. As described above, the conveying unit driver 143 may include a motor or an actuator. The second collimator driver 153 may operate the second collimator 152 according to the control instructions of the first CPU 170. The operation of the second collimator 152 may include position movement in a vertical direction or lateral direction or changing the size of the transmission hole 153b, for example.

The first storage unit 180 may store various information to control the CT scanner 100. The first storage unit 180 may be installed inside or outside the external housing 98 of the CT scanner 100. The first storage unit 180 may be a semiconductor memory device or a magnetic disk memory device and may store data temporarily or non-temporarily.

Figure 8:
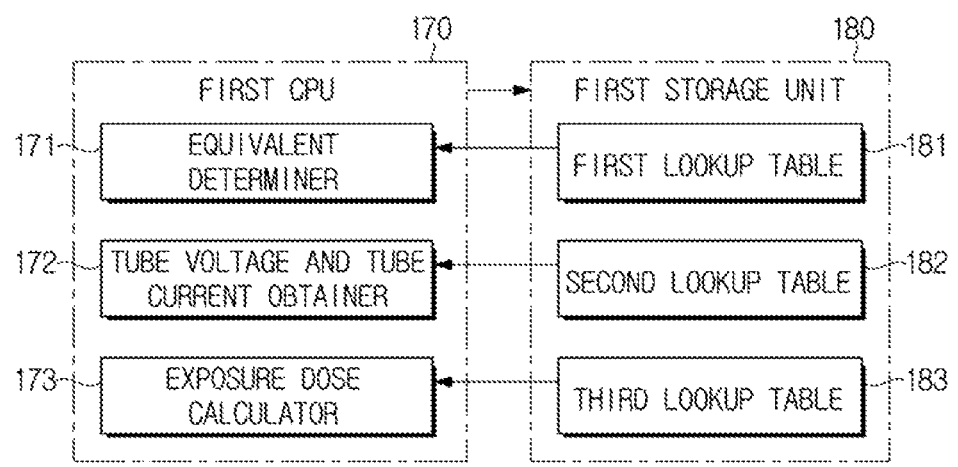
FIG. 8 is a view of a configuration of a central processing unit (CPU) and a storage unit according to an exemplary embodiment.

FIG. 8 is a view of a configuration of a CPU and a storage unit according to an exemplary embodiment. The first CPU 170 may include an equivalent determiner 171, a tube voltage and tube current obtainer 172, and an exposure dose calculator 173, as illustrated in FIG. 8. The equivalent determiner 171, the tube voltage and tube current obtainer 172, and the exposure dose calculator 173 may be implemented by a plurality of semiconductor devices that are physically separated from each other or may be integrated on a single semiconductor device.

The first storage unit 180 may store reference data required for control, for example, first data, second data, and third data. In detail, the first storage unit 180 may store the first data, the second data, and the third data as first, second, and third lookup tables 181 through 183, as illustrated in FIG. 8. The first lookup table 181 may be a set of data regarding the relationship between the tube voltage, the attenuation information, and the equivalent. The second lookup table 182 may be a set of data regarding the relationship between the tube voltage, the equivalent, and the tube current of the radiographic rays. The third lookup table 183 may be a set of data regarding the relationship between the tube voltage, the tube current, and the exposure dose of the radiographic rays. The first through third lookup tables 181 through 183 may be obtained in advance, by empirically measuring the data using separate experiments or by performing an arithmetic operation using a separate physical formula.

The equivalent determiner 171 of the first CPU 170 may determine the equivalent corresponding to the object based on the obtained radiographic image. In detail, the first CPU 170 may determine one or more equivalents that correspond to all or part of the object using the attenuation information regarding all or part of the object based on signals output from the radiographic detector 150. The equivalent determiner 171 may determine the equivalent corresponding to the object using the radiographic image captured by the CT scanner 100 or using the radiographic image captured by another radiographic imaging apparatus, such as a DR apparatus or another CT apparatus.

The intensity of the radiographic rays transmitting the object may be obtained using the following Equation 1:

$$I = I_o e^{-\mu t}$$

where I is an intensity of the radiographic rays detected by the radiographic detector 150, $I_o$ is an intensity of the radiographic rays radiated by the radiographic tube 120, μ is an attenuation coefficient according to characteristics of an object, and t is a distance which the radiographic rays penetrate in the object, i.e., a width of the object.

If an attenuation rate $(I/I_o)$ of the object and an attenuation rate $(I_e/I_{eo})$ of the equivalent are the same, an exponential part $-\mu t$ of the object and an exponential part $-\mu_e t_e$ of the equivalent may also be the same. If equivalents are the same and attenuation coefficients $\mu_e$ of the equivalents are constant, widths $t_e$ of the equivalents vary according to the type of the object. In other words, the equivalents having different widths $t_e$ may correspond to different objects. One or more equivalents corresponding to all or part of the object may be determined according to the width $t_e$ using the above principle. This may be regarded as converting all or part of the object based on the widths of the equivalents. If the equivalents are WEOs, components inside the object may be converted based on water.

The equivalent determiner 171 of the first CPU 170 may determine one or more equivalents having the widths $t_e$ corresponding to all or part of the object, as described above. The equivalent determiner 171 may determine one or more equivalents according to the tube voltage and the attenuation information by referring to the first lookup table 181 that is the previously-obtained first data regarding the relationship between the tube voltage, the attenuation information, and the equivalent.

Figure 9:
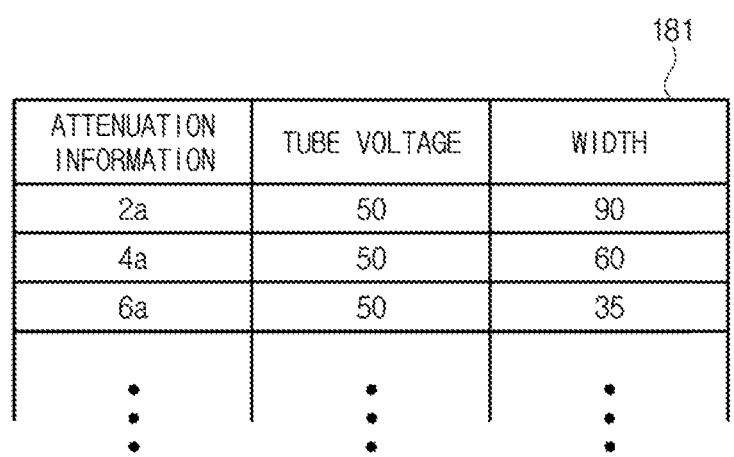
FIG. 9 is a view of first data regarding the relationship between a tube voltage, attenuation information and an equivalent of radiographic rays.

FIG. 9 is a view of first data regarding the relationship between a tube voltage, attenuation information and an equivalent of radiographic rays. FIG. 9 is drawn for convenience of explanation, and values shown in FIG. 9 may be different from actual measurement values. In the table of FIG. 9, a first column is a radiographic ray intensity that is an example of the attenuation information, wherein 2a is twice a reference value a, and 4a is four times the reference value a. In the table of FIG. 9, a second column is a tube voltage (kVp), and a third column is a width (cm) of a corresponding equivalent. FIG. 9 shows only the result of the tube voltage of 50 kVp. However, the first lookup table 181 may further include information regarding the different tube voltages. The equivalent determiner 171 may determine the equivalent having a width of 60 cm when the radiographic ray intensity is 4a and the tube voltage is 50 kVp. The first lookup table 181 may be drawn based on data that is empirically obtained by irradiating the radiographic rays onto a predetermined object and a WEO, respectively.

Figure 10:
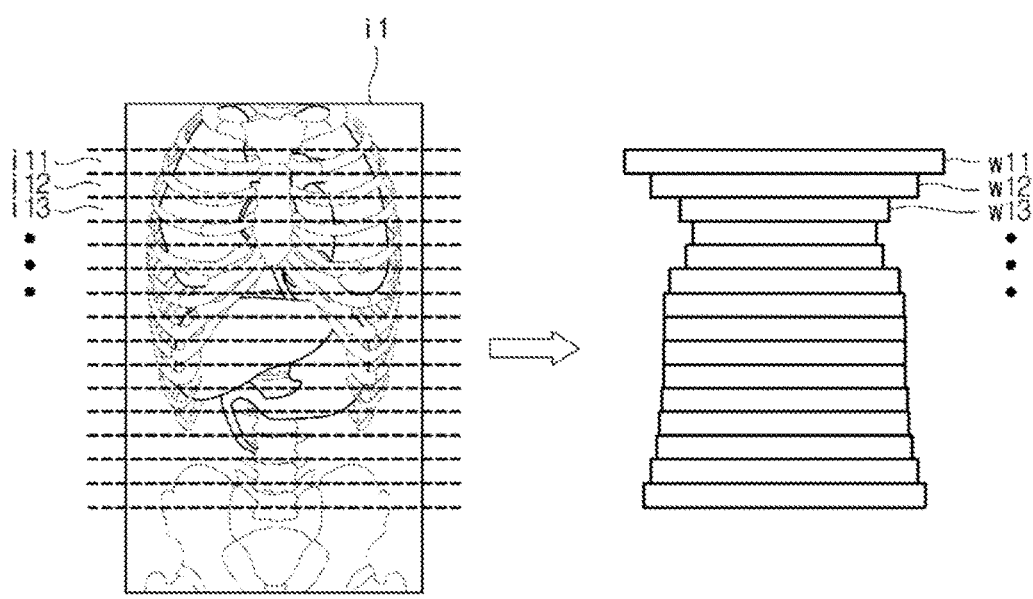
FIG. 10 is a view of an equivalent corresponding to each zone of an object.

FIG. 10 is a view of an equivalent corresponding to each zone of an object. Referring to FIG. 10, the equivalent determiner 171 may partition a radiographic image it into a plurality of predetermined, detailed zones i11, i12, i13, etc., and then may determine equivalents w11, w12, w13, etc., corresponding to the detailed zones i11 through i13. In this case, widths $t_e$ of the equivalents w11 through w13 corresponding to the detailed zones i11 through i13 may be different from each other according to the types of components inside the object corresponding to the detailed zones i11 through i13. For example, when one detailed zone is an image obtained when the radiographic rays are transmitted by lungs, the width of an equivalent corresponding to the one detailed zone may be smaller than a width of another detailed zone that is an image obtained when the radiographic rays are transmitted by internal organs.

The tube voltage and tube current obtainer 172 may acquire one or more tube voltages and tube currents using quality of radiographic images to be obtained and determined equivalents when the equivalents regarding all of the object or the plurality of detailed zones i11 through i13 are determined.

The quality of the radiographic image may be input by the user using an input unit 212 of the workstation 200 or an input means, such as a keyboard or a mouse disposed on the CT scanner 100. The quality of the radiographic image may include a noise ratio that is a degree of noise in an image, resolution, a contrast ratio, and/or sharpness. The quality of the radiographic image may be a numerical index, e.g., 1, 2, 3, etc., which is determined in advanced based on at least one of a noise ratio, resolution, a contrast ratio, and sharpness. In order the user to select the quality of the image, an output unit 214 of the workstation 200, for example, a display may display a plurality of options regarding the quality of the radiographic image on a screen. The user may move a focus of the image by moving a cursor using the mouse or manipulating an arrow button on the keyboard and thus may select one among the plurality of options. The plurality of options displayed on the output unit 214 may include texts and/or images. The user may select quality of one radiographic image or quality of a plurality of radiographic images as needed.

When the first CPU 170 or the user determines a level of quality of the radiographic image, the tube voltage and tube current obtainer 172 may acquire one or more tube voltages and tube currents according to the determined quality level. The tube voltage and tube current obtainer 172 may acquire one or more sets of a plurality of tube voltages and tube currents for each one or more equivalents.

Figure 11:
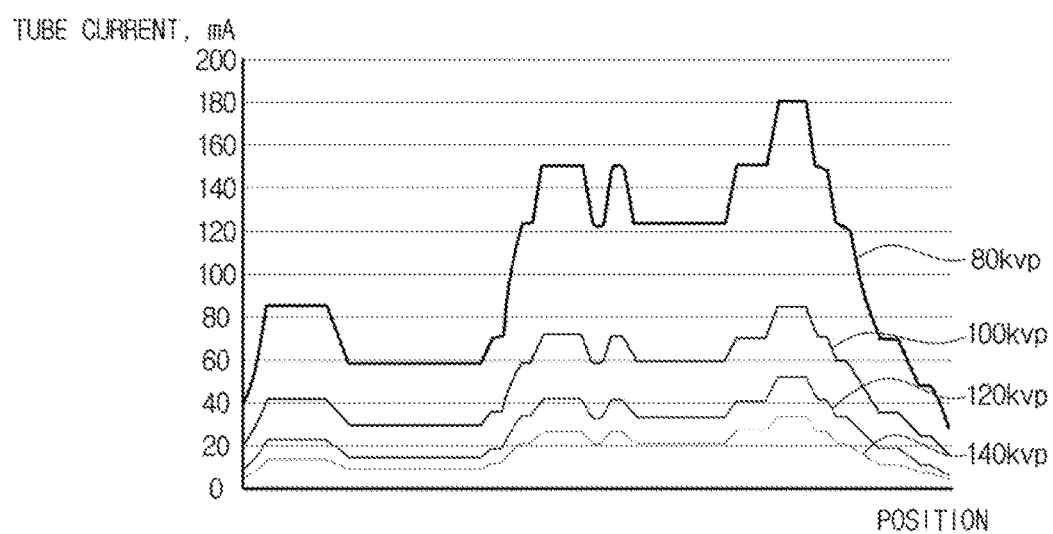
FIG. 11 is a view of the relationship between a tube voltage, an equivalent, and a tube current.

FIG. 11 is a view of the relationship between a tube voltage, an equivalent, and a tube current, and FIG. 12 is a view of the obtained tube voltage and tube current according to an exemplary embodiment. The y-axis of FIG. 11 may be a tube current, and the x-axis of FIG. 11 may be a distance from a particular portion of the object. FIG. 11 illustrates the tube currents according to tube voltages 80 kVp, 100 kVp, 120 kVp, and 140 kVp, as an example. The tube voltage and tube current obtainer 172 may determine one or more tube voltages and tube currents for each of the plurality of equivalents w11 through w13 based on the relationship between the tube voltage, the equivalent, and the tube current, as illustrated in FIG. 11, thereby generating a plurality of sets of tube voltages and tube currents, as illustrated in FIG. 12. One or more sets of tube voltages and tube currents may be determined for each of the equivalents w11 through w13.

According to an exemplary embodiment, the tube voltage and tube current obtainer 172 may determine one or more sets of tube voltages and tube currents based on the quality level of the image by referring to the second lookup table 182 that is the second data. When there is a plurality of equivalents, a plurality of sets of tube voltages and tube currents may be determined. The second lookup table 182 may be obtained empirically, by empirically measuring degrees of tube voltages and tube currents to be applied to obtain a radiographic image having particular quality from a particular equivalent. The second lookup table 182 may include information regarding one or more attainable tube voltages and tube currents when a predetermined equivalent and the quality of the radiographic image are determined.

The second lookup table 182 may be stored in the first storage unit 180 in a similar shape to the first lookup table 181 illustrated in FIG. 11.

When one or more tube voltages and tube currents are obtained, the exposure dose calculator 173 may calculate exposure doses corresponding to one or more tube voltages and tube currents using the obtained one or more tube voltages and tube currents. The exposure dose calculator 173 may select a tube voltage and a tube current having a smallest exposure dose of the obtained tube voltages and tube currents after the exposure doses are calculated.

Figure 13:
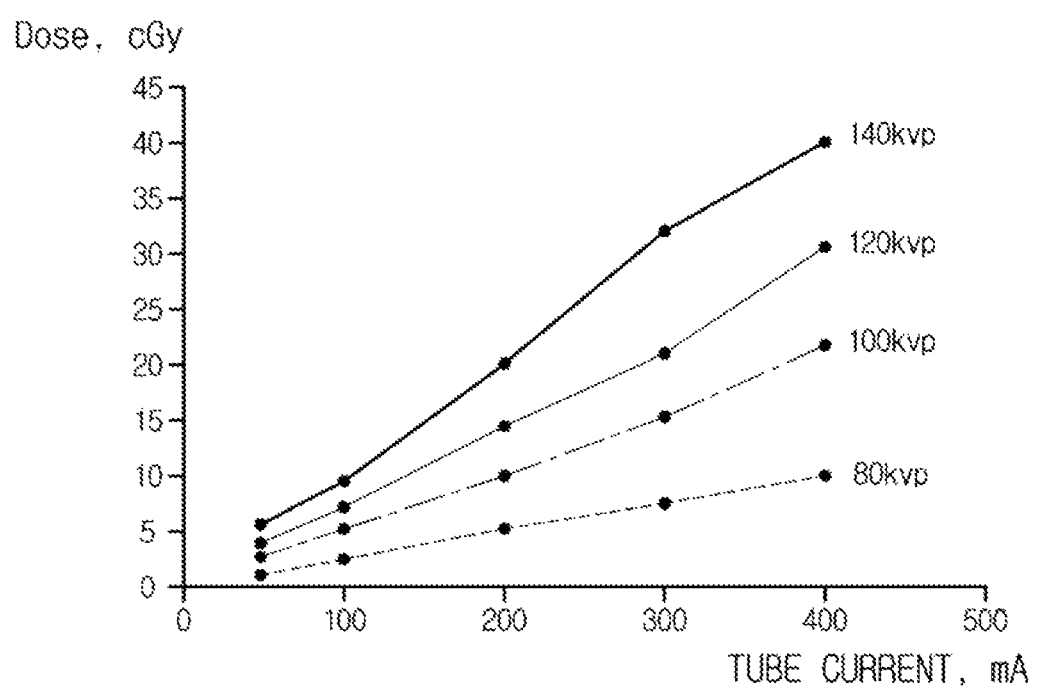
FIG. 13 is a view of the relationship between the tube voltage, the tube current, and an expected exposure dose of the radiographic rays.

FIG. 13 is a view of the relationship between the tube voltage, the tube current, and an expected exposure dose of the radiographic rays. The x-axis of FIG. 13 is a tube current, and the y-axis of FIG. 13 represents an exposure dose. Referring to FIG. 13, the exposure dose that represents radiographic rays to which the object 99 is exposed, may increase as tube voltages (see 80 kVp, 100 kVp, 120 kVp, and 140 kVp) increase or tube currents increase. In more detail, the exposure dose increases in proportion to an n square ($2 \leq n \leq 3$) of a change amount of the tube voltages. The exposure dose may grow in arithmetical progression in proportion to an increase in tube currents. Thus, the exposure dose that represents radiographic rays to which the object 99 is exposed, varies according to the sizes of the tube voltages and the tube currents. The exposure dose calculator 173 may calculate an exposure dose according to the tube voltages and the tube currents and may detect a smallest exposure dose of the calculated exposure doses and then may select a tube voltage and a tube current that correspond to the detected exposure dose. In order to calculate the exposure doses according to the tube voltages and the tube currents, the exposure dose calculator 173 may refer to the third lookup table 183 that is the third data stored in the first storage unit 180.

FIG. 14 is a view of an operation of selecting a third lookup table and a smallest exposure dose of expected exposure doses. As illustrated in FIG. 14, the third lookup table 183 may include data regarding the relationship between the tube voltage, the tube current, and the expected exposure dose. The unit of the tube voltage is kVp, and the unit of the tube current is mA. The unit of the exposure dose is centigray (cGy). For example, according to the third lookup table 183 of FIG. 14, when the tube voltage is 80 kVp and the tube current is 180 mA, the exposure dose calculator 173 may determine that the expected exposure dose is 3 cGy. When one or more expected exposure doses are determined for one or more tube voltages and tube currents determined by the tube voltage and tube current obtainer 172 in this manner, the exposure dose calculator 173 may select a smallest expected exposure dose 184 of the determined exposure doses and may select a tube voltage of 100 kVp and a tube current of 85 mA that correspond to the selected expected exposure dose of 2 cGy.

If the tube voltage and the tube current corresponding to the smallest exposure dose are selected, the first CPU 170 may control the CT scanner 100 to recommend the selected tube voltage and tube current to the user. According to an exemplary embodiment, the first CPU 170 may control the CT scanner 100 to display the selected tube voltage and tube current to the user and to recommend the selected tube voltage and tube current. For example, the first CPU 170 may transmit the selected tube voltage and tube current to the workstation 200 through the first communicator 192 and the second communicator 211, and the workstation 200 may provide the selected tube voltage and tube current to the user through the output unit 214, such as the display, and may recommend the selected tube voltage and tube current.

The user may select the tube voltage and tube current recommended through the output unit 214 using the input unit 212 disposed in the workstation 200. If the user does not select the provided tube voltage and tube current, the user may input the user's desired tube voltage and tube current through the input unit 212. When the user selects the provided tube voltage and tube current or inputs new tube voltage and tube current, the first CPU 170 may generate control instructions for controlling the radiographic radiation source 110 according to the selected tube voltage and tube current or the newly-input tube voltage and tube current and may transmit the control instructions to the radiographic radiation source 110 or the tube driver 121.

The tube driver 121 may apply the selected tube voltage and tube current or the newly-input tube voltage and tube current to the radiographic tube 120 of the radiographic radiation source 110 according to the control instructions, and the radiographic tube 120 may generate radiographic rays according to the applied tube voltage and tube current and may irradiate the object 99 with the generated radiographic rays. The generated radiographic rays may pass through the object 99 inside the bore 141 and may be absorbed by a tissue inside the object 99 or transmit the tissue inside the object 99. The radiographic detector 150 may receive the radiographic rays transmitted through the object 99 and may output electrical signals, and the image processor 191 may generate a radiographic image based on the electrical signals output from the radiographic detector 150. The generated radiographic image may be provided to the user through the output unit 214.

Figure 15:
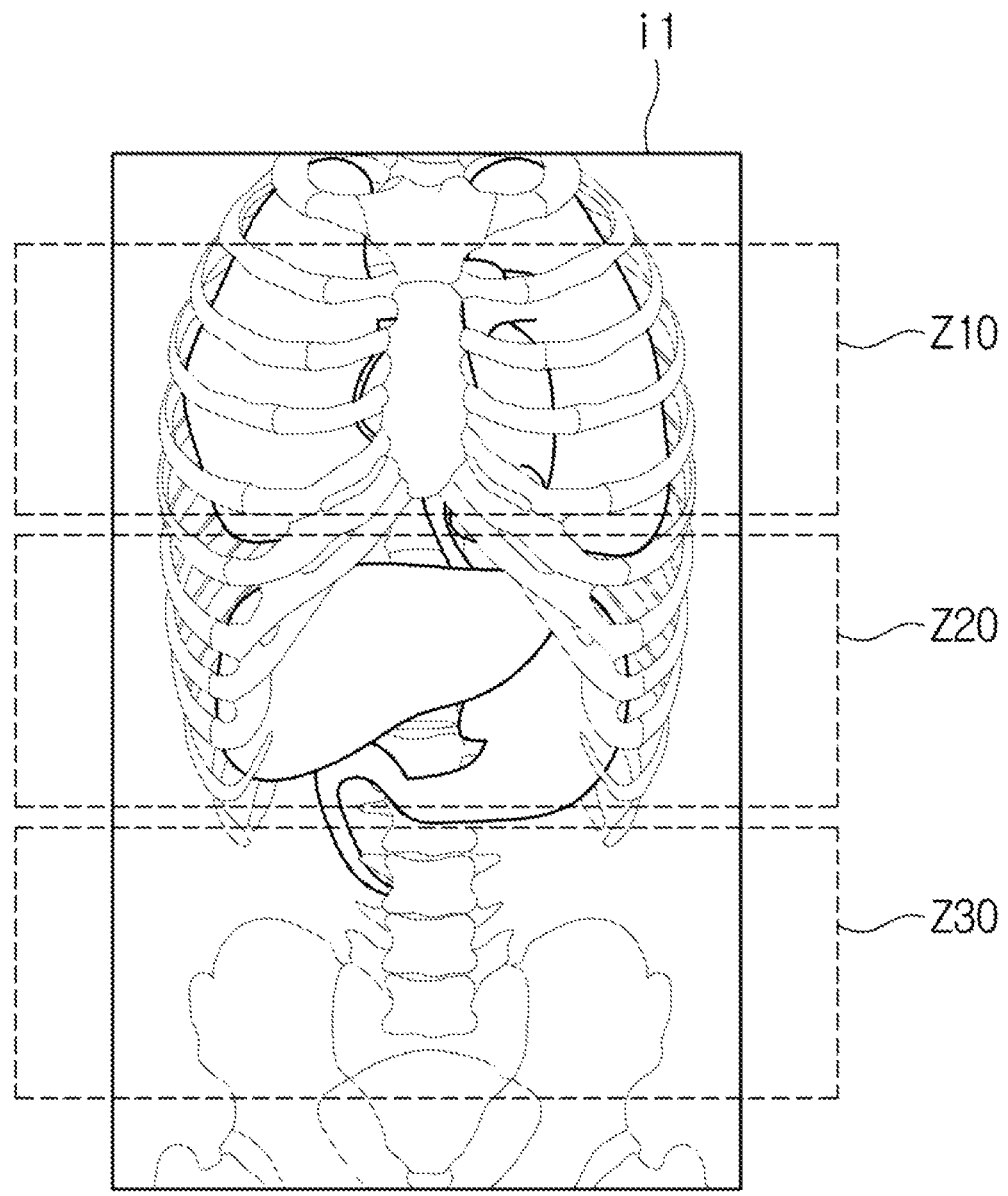
FIG. 15 is a view of an example in which a radiographic image is partitioned into zones.
Figure 16:
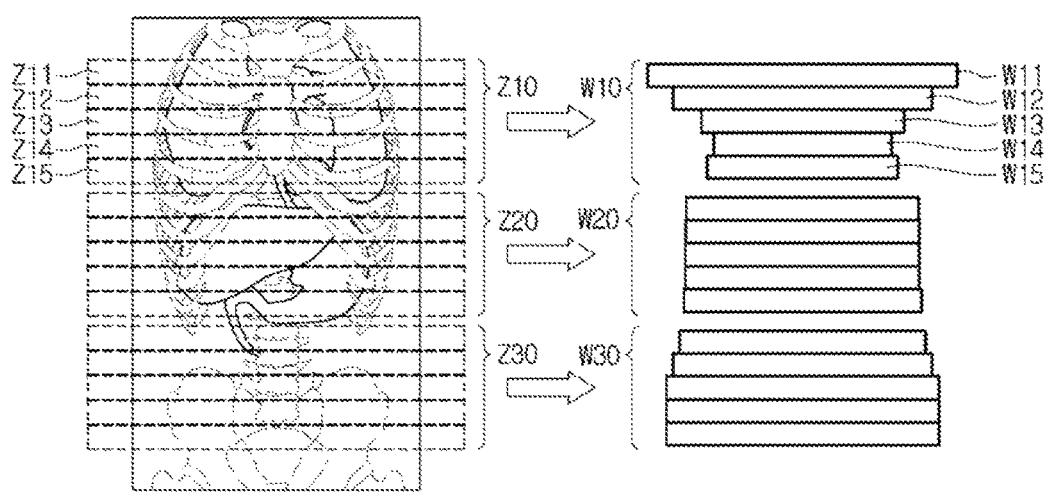
FIG. 16 is a view of an example in which the equivalent is determined in each zone.
Figure 17:
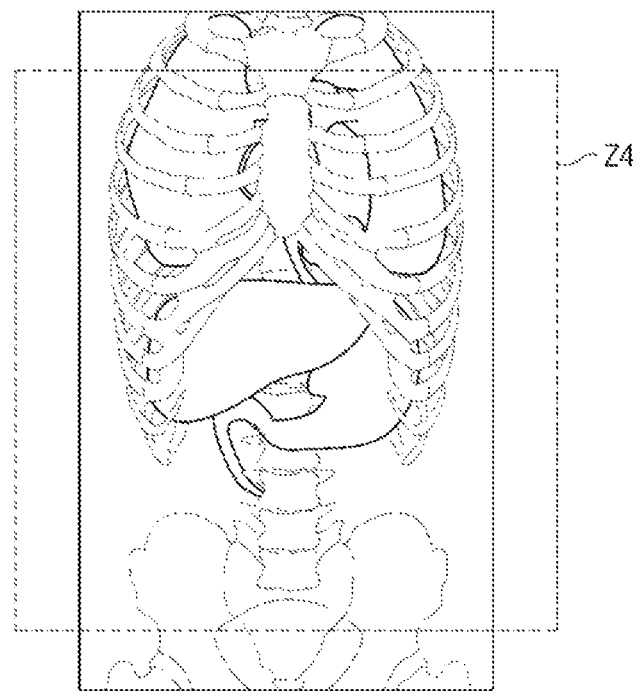
FIGS. 17 and 18 are views of exemplary embodiments in which an equivalent is determined in zones and then an image of the object is captured according to the determined equivalent.
Figure 18:
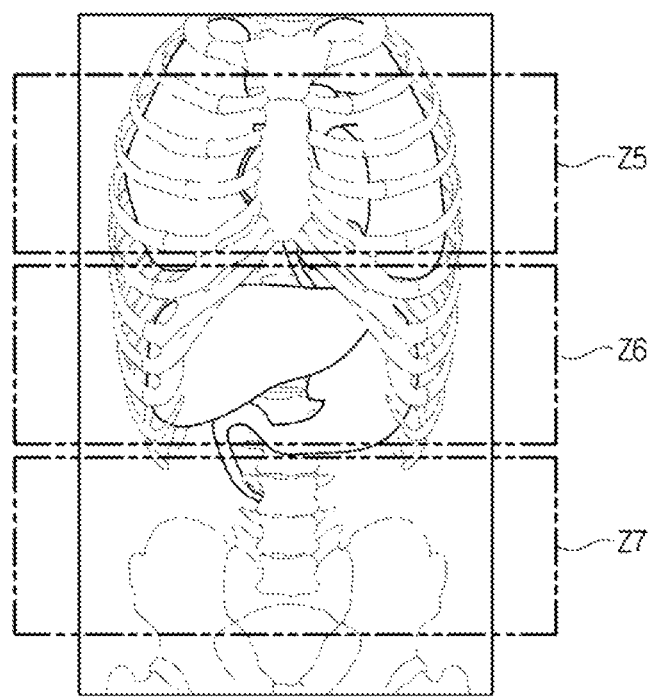

An example in which a plurality of equivalents is determined according to a plurality of zones of a radiographic image and then radiographic imaging is performed is described below with reference to FIGS. 15 through 18. FIG. 15 is a view of an example in which a radiographic image is partitioned into a plurality of zones, and FIG. 16 is a view of an example in which the equivalent is determined in each zone. FIGS. 17 and 18 are views of exemplary embodiments in which an equivalent is determined in each of a plurality of zones and then an image of the object is captured according to the determined equivalent.

As illustrated in FIG. 15, a radiographic image it may be partitioned into a plurality of zones, for example, a first zone z10, a second zone z20, and a third zone z30. Partitioning the zones z10 through z30 may be performed arbitrarily or according to predetermined settings by the first CPU 170 or by the user. The user may partition the zones z10 through z30 through the input unit 212 of the workstation 200. The zones z10 through z30 may be obtained by partitioning only part of the radiographic image i1 (not all of the radiographic image i1).

As illustrated in FIG. 16, the equivalent determiner 171 may determine equivalents w10 through w30 separately in each of the zones z10 through z30. In other words, the equivalent determiner 171 may determine the first equivalent w10 corresponding to the first zone z10, the second equivalent w20 corresponding to the second zone z20, and the third equivalent w30 corresponding to the third zone z30. Determining the equivalents w10 through w30 corresponding to the zones z10 through z30 may be performed by referring to the first lookup table 181. The equivalents w10 through w30 may be equivalents corresponding to all of the zones z10 through z30. The equivalents w11, w12, w13, w14, and w15 may be a plurality of equivalents corresponding to a plurality of detailed zones z11, z12, z13, z14, and z15 obtained by additionally partitioning each zone, for example, the first zone z10, as illustrated in FIG. 16. Although not shown, the remaining zones z20 and z30 may also be partitioned into a plurality of detailed zones, and a plurality of equivalents corresponding to the plurality of detailed zones may also be obtained.

If the equivalents are obtained in this way, the tube voltage and tube current obtainer 172 may acquire one or more tube voltages and tube currents in each of the equivalents w10 through w30 using the quality of a radiographic image to be obtained and the equivalents w10 through w30. As described above, the second lookup table 182 that is the second data may be used to obtain the tube voltage and tube current. The exposure dose calculator 173 may calculate the exposure dose of each of the acquired one or more tube voltages and tube currents. In order to calculate the exposure doses according to the tube voltage and tube current, the exposure dose calculator 173 may also refer to the third lookup table 183 stored in the first storage unit 180.

According to an exemplary embodiment, after the exposure doses are calculated, the exposure dose calculator 173 may select a smallest exposure dose of the calculated exposure doses and may select a tube voltage and a tube current that correspond to the selected exposure dose. In other words, a tube voltage and a tube current having the smallest exposure dose may be selected of tube voltages and tube currents relating to a zone z4 (illustrated in FIG. 17), including the first through third zones z10 and z30. The selected tube voltage and tube current may be displayed to the user, as a recommendation, by control of the first CPU 170. If the user confirms radiographic ray irradiation by the recommended tube voltage and tube current, all or part of the object 99 corresponding to the zone z4 including the first through third zones z10 through z30 may be irradiated with the radiographic rays corresponding to the tube voltage and the tube current selected by the exposure dose calculator 173 so that radiographic imaging may be performed. In other words, the same tube voltage and tube current may be applied to the radiographic tube 120 to image the entire zone z4.

According to another exemplary embodiment, after the exposure doses are calculated, the exposure dose calculator 173 may select a tube voltage and a tube current having the smallest exposure dose in each zone, for example, in each of the first through third zones z10 through z30. Thus, a plurality of tube voltages and tube currents corresponding to the partitioned zones z10 through z30 may be selected, and the plurality of selected tube voltages and tube currents may be displayed to the user by control of the first CPU 170. If the user confirms radiographic ray irradiation by the recommended plurality of selected tube voltages and tube currents, the radiographic rays corresponding to the tube voltage and tube current selected in each of zones z5, z6, and z7 (see FIG. 18) of the object 99 corresponding to the first through third zones z10 through z30, may be radiated. In other words, in order to image the zones z5 through z7, different tube voltages and tube currents may be applied to the radiographic tube 120 in each of the zones z5 through z7.

The above-described functions of the first CPU 170 and the first storage unit 180 may also be performed by the second CPU 210 and the second storage unit 213 of the workstation 200.

The first communicator 192 may transmit and/or receive data to and/or from the second communicator 211 of the workstation 200. The first communicator 192 may include at least one of a wired network device, such as a local area network (LAN) card, and a wireless network device, such as a wireless communication chip.

The power source 193 may supply power for each configuration of the CT scanner 100. The power source 193 may be implemented by a power generator disposed in the CT scanner 100 or a capacitor for storing electric energy supplied from an external common-use power source.

The CT scanner 100 may further include an input means, such as a keyboard or a mouse, or an output means, such as a display or a speaker, as needed. The input means or output means may be installed outside the external housing 98. The user may also instruct activation of the CT scanner 100 or input quality of an image to be obtained using the input means of the CT scanner 100. The user may also obtain information regarding the selected tube voltage and tube current or receive an image of the object 99 using the output means of the CT scanner 100.

Hereinafter, the workstation 200 is described in detail below with reference to FIGS. 2 and 4. Referring to FIGS. 2 and 4, the workstation 200 may receive various instructions from the user and may perform various processing according to the input instructions. The workstation 200 may provide various pieces of information, such as various processing results or a radiographic image captured by the CT scanner 100, to the user. The workstation 200 may include the second CPU 210, the communicator 211, the input unit 212, the second storage unit 213, and the output unit 214.

The second CPU 210 may perform arithmetic operation and processing and may generate control instructions, thereby controlling an operation of the CT scanner 100 or the workstation 200. According to an exemplary embodiment, the second CPU 210 may perform a function of the first CPU 170 of the CT scanner 100. The first CPU 170 may also be omitted. According to another embodiment, the above-described first CPU 170 may perform a function of the second CPU 210. The second CPU 210 may be implemented using a semiconductor chip.

The second communicator 211 may transmit/receive data to/from the first communicator 192 of the CT scanner 100. The second communicator 211 may be a wired network device, such as an LAN card, or a wireless network device, such as an antenna or a wireless communication chip. The input unit 212 may receive various pieces of information from the user. For example, the input unit 212 may receive setting values of quality of a radiographic image to be captured, from the user. The input unit 212 may include various input means, such as a keyboard, a mouse, a keypad, a track ball, a track pad, a touch pad, and a touch screen.

The second storage unit 213 may store various pieces of information transmitted by the second CPU 210. The second storage unit 213 may store the first through third lookup tables 181 through 183 that are the first through third data. The second CPU 210 may read the first through third data from the second storage unit 213 and may determine the equivalent, the tube voltage, the tube current, and the exposure dose in the same or similar manner as or to the above-described manner using the read first through third data as needed. The first storage unit 180 may also be omitted. The second storage unit 213 may also be implemented using at least one of a semiconductor memory device and a magnetic disk memory device. The output unit 214 may provide various pieces of information, for example, the radiographic image or the selected tube voltage and tube current, to the user. The output unit 214 may include various output means that may display or transmit information to the user, such as a display, a speaker, and an illumination device.

The workstation 200 may be omitted according to an exemplary embodiment.

A DR apparatus that is another example of a radiographic imaging apparatus is described in detail below with reference to FIGS. 19 and 20. Parts of the DR apparatus may be the same as or similar to the parts of the above-described CT apparatus. Thus, a repeated detailed description of the parts of the DR apparatus is omitted.

Figure 19:
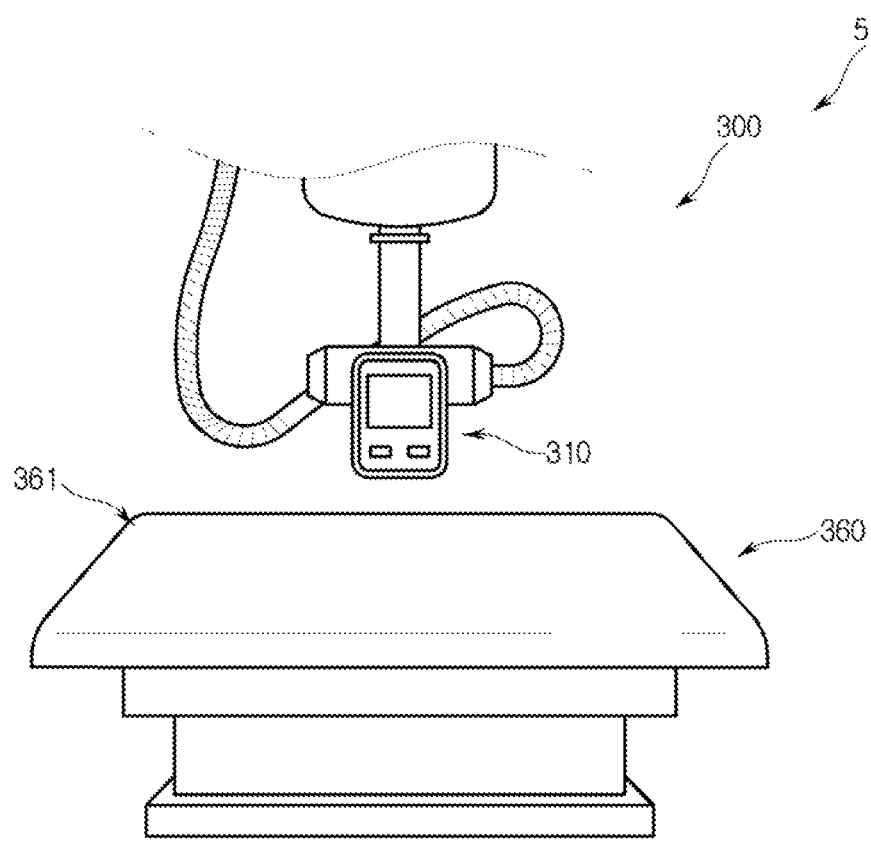
FIG. 19 is a view of a DR imaging apparatus according to an exemplary embodiment.
Figure 20:
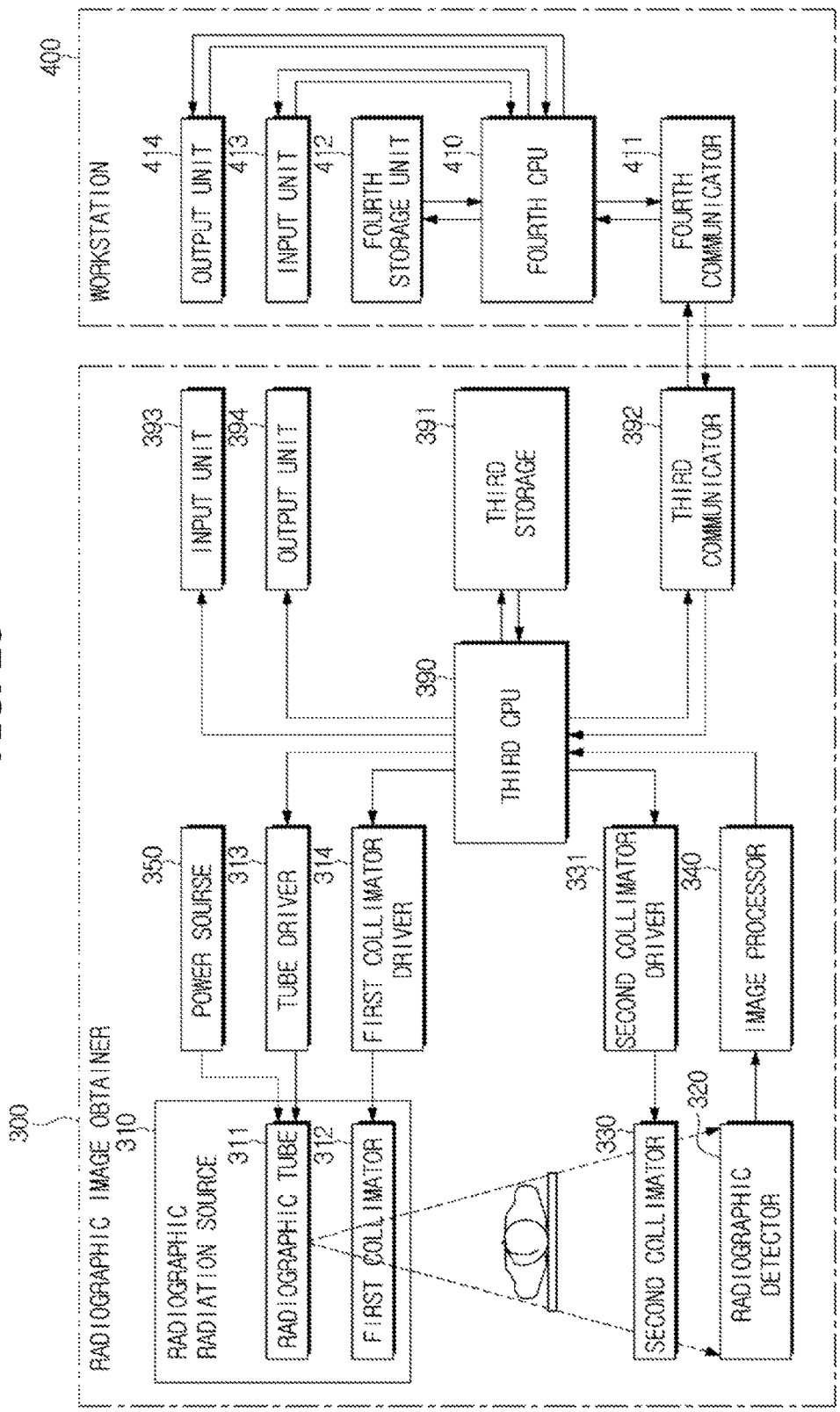
FIG. 20 is a view of a configuration of the DR imaging apparatus according to an exemplary embodiment.

Referring to FIGS. 19 and 20, a DR apparatus 5 may include a radiographic image obtainer 300 and a workstation 400 that may be connected to the radiographic image obtainer 300 via a wired communication network or a wireless communication network.

The radiographic image obtainer 300 may include a radiographic radiation source 310 that irradiates the object 99 with radiographic rays, and a radiographic detector 320. The radiographic radiation source 310 may be moved according to the user's manipulation. The radiographic radiation source 310 may include a radiographic tube 311 and a first collimator 312. The radiographic tube 311 may generate radiographic rays in the same manner as the above-described with reference to the CT scanner 100 and then may irradiate the object 99 with the generated radiographic rays. The object 99 may be irradiated with different radiographic rays according to the tube voltage and tube current applied by a power source 350. In the same manner as the above-described, the first collimator 312 may adjust an irradiation range and an irradiation direction of the radiographic rays generated in the radiographic tube 311. The object 99 may be placed on a holding surface 361 on a table 360. A second collimator 330 and a radiographic detector 320 may be embedded in the table 360. The radiographic detector 320 may output electrical signals corresponding to the received radiographic rays in the same manner as the above-described with reference to the CT scanner 100. The radiographic detector 320 may be moved in a predetermined direction. The second collimator 330 may allow only unscattered, appropriate radiographic rays transmitted through the object 99 to be transmitted to the radiographic detector 320 in the same manner as the above-described. According to an exemplary embodiment, the radiographic radiation source 310 and the radiographic detector 320 may be installed on both ends of a C-shaped C-arm module (not shown). In this case, the object 99 may be disposed between both ends of the C-arm module, and the C-arm module may perform radiographic imaging while rotating about the object 99.

The radiographic image obtainer 300 may include a third CPU 390 that controls an operation of the radiographic image obtainer 300 and a third storage unit 391 that stores various pieces of information to control the radiographic image obtainer 300. The third CPU 390 may determine one or more equivalents of the object 99 using attenuation information and may obtain a tube voltage and a tube current for each of the equivalents according to setting values of quality of the received radiographic image. The third CPU 390 may determine one or more equivalents using a first lookup table that is first data. The third CPU 390 may obtain one or more tube voltage and tube current according to quality of the radiographic image using a second lookup table that is second data. Furthermore, the third CPU 390 may determine exposure doses according to each tube voltage and tube current using one or more tube voltage and tube current. The third CPU 390 may determine the exposure doses using a third lookup table that is third data. Furthermore, the third CPU 390 may select a smallest exposure dose of the determined exposure doses and may select a tube voltage and a tube current that correspond to the selected exposure dose. The selected tube voltage and tube current may be provided to the user through the output unit 394 of the radiographic image obtainer 300 or the output unit 414 of the workstation 400. The user may determine whether to perform radiographic imaging by radiating the radiographic rays according to the selected tube voltage and tube current using the input unit 393 of the radiographic image obtainer 300 and the input unit 413 of the workstation 400. The third storage unit 391 may store the first lookup table, the second lookup table, and the third lookup table described above.

The radiographic image obtainer 300 may further include a tube driver 313 for driving the radiographic tube 311, a first collimator driver 314 for driving the first collimator 312, a second collimator driver 331 for driving the second collimator 330, an image processor 340 that generates a radiographic image based on electrical signals output from the radiographic detector 320 and performs various image processing on the generated radiographic image, and a communicator 392 for communication with the workstation 400, as needed. The radiographic image obtainer 300 may further include an input unit 393, such as a keyboard, and an output unit 394, such as a display. Setting values of quality of the radiographic image may be input through the input unit 393. The above-described configuration may be the same or almost similar to the above-described CT apparatus 4.

The workstation 400 may include a fourth CPU 410, a fourth communicator 411, a fourth storage unit 412, an input unit 413, and an output unit 414. The fourth CPU 410 may control an operation of the workstation 400 and may perform a function of the third CPU 390. For example, the fourth CPU 410 may perform a function of determining an equivalent, acquiring a tube voltage and a tube current and obtaining an exposure dose and then selecting a smallest exposure dose. The fourth storage unit 412 may also perform a function of the third storage unit 391. The fourth communicator 411 may perform wired communication or wireless communication with the third communicator 392. The input unit 413 may receive various instructions from the user, and whether to select a tube voltage and a tube current by the third CPU 390 or the fourth CPU 410 may be input to the input unit 413. The output unit 414 may provide the tube voltage and tube current selected by the third CPU 390 or the fourth CPU 410 in the form of an image or a sound to the user.

The described above CT apparatus 4 and the DR apparatus 5 are examples of the radiographic imaging apparatus 1. However, the radiographic imaging apparatus 1 is not limited thereto. The radiographic imaging apparatus 1 may be an FFDM apparatus, for example. In addition, the radiographic imaging apparatus 1 may include any imaging apparatus that captures a radiographic image by applying a tube voltage and a tube current to a radiographic tube and detects radiographic rays.

FIGS. 21 to 24 are flowcharts illustrating a method of controlling the radiographic imaging apparatus according to an exemplary embodiment. The described above with reference to FIGS. 1 to 20 is applicable here and is not repeated.

Figure 21:
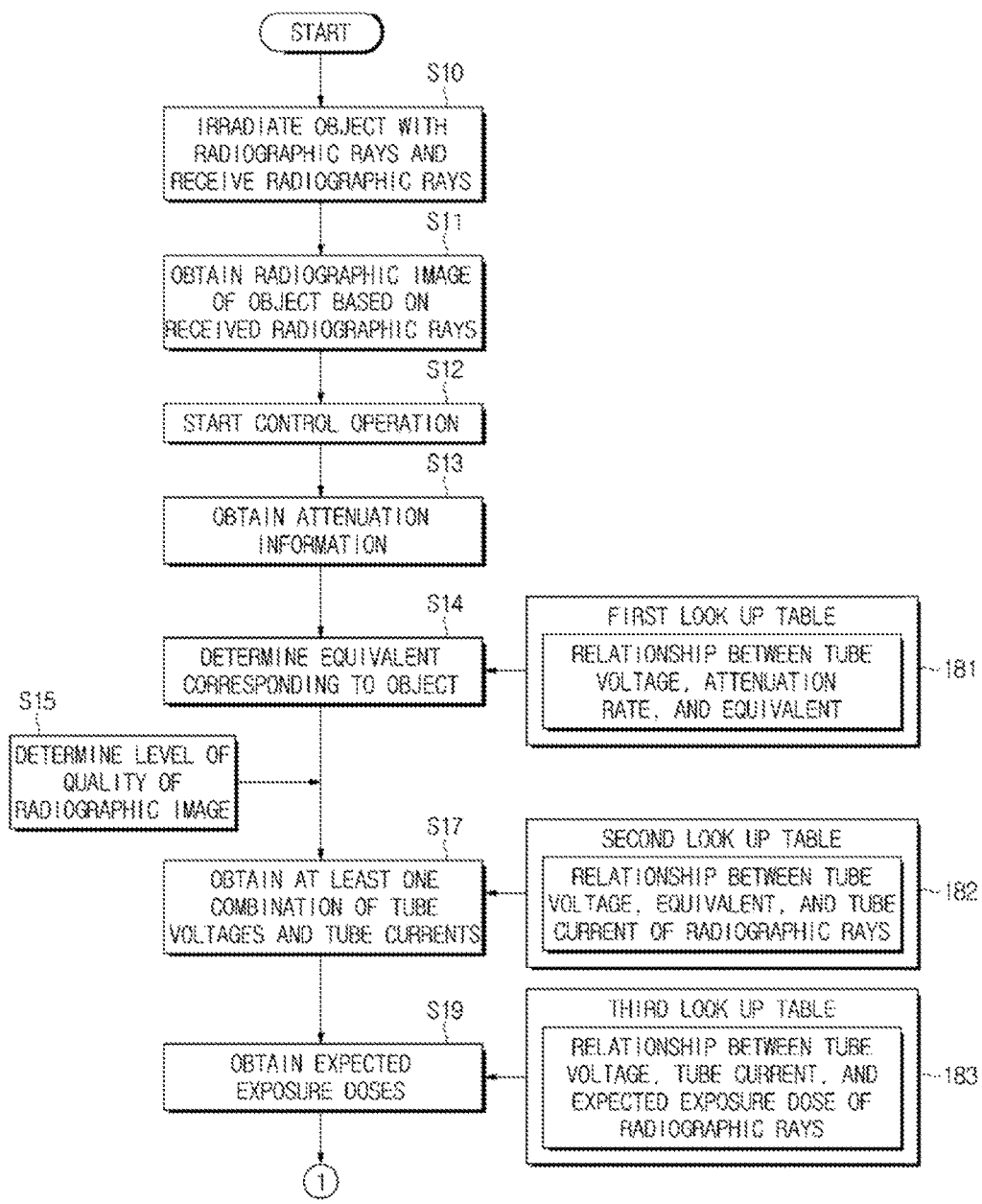
FIGS. 21 and 22 are flowcharts of a method of controlling a radiographic imaging apparatus, according to an exemplary embodiment.
Figure 22:
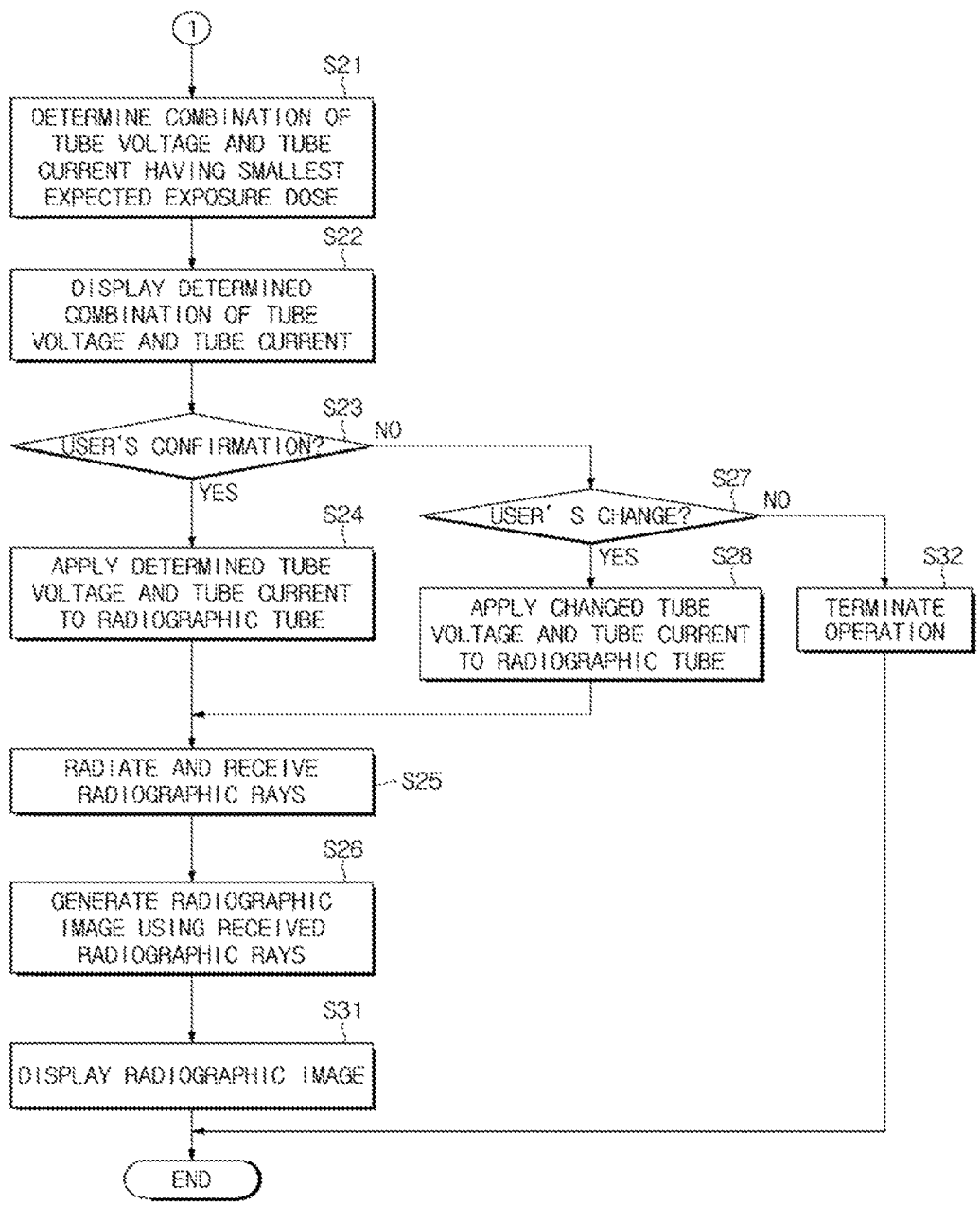

With reference to FIGS. 21 and 22, a radiographic radiation source of a first radiographic imaging apparatus irradiates an object with radiographic rays, and the irradiated radiographic rays may be received by a radiographic detector (operation S10). The radiographic rays transmitted through the object may be attenuated according to characteristics of a material inside the object, for example, density. The radiographic detector may receive the radiographic rays and may output electrical signals. The first radiographic imaging apparatus obtains a first radiographic image corresponding to the received radiographic rays based on the received radiographic rays (operation S11). For example, the first radiographic image may be an image obtained with a reduced radiation amount, by appropriately controlling at least one of the tube voltage, tube current, and a tube collimator. As another example, the first radiographic image may be an image of the object obtained during a previous visit to the hospital.

If the first radiographic image is obtained, a second radiographic imaging apparatus starts an operation for performing the method of controlling the radiographic imaging according to the user's manipulation or predetermined settings (operation S12).

The first and second radiographic imaging apparatuses may include any radiographic apparatus described above. The second radiographic imaging apparatus that performs the method of controlling the radiographic imaging apparatus and the first radiographic imaging apparatus that captures the radiographic image in operations S10 and S11 described above may be the same as or different from each other. The second radiographic imaging apparatus and the first radiographic imaging apparatus may be the same type of apparatuses or different types of apparatuses. If the second radiographic imaging apparatus that is different from the first radiographic imaging apparatus is used, the first radiographic image obtained in operations S10 and S11 may be transmitted to the second radiographic imaging apparatus using by a wire or wirelessly or via a portable storage device. For example, the first radiographic image obtained by the first radiographic imaging apparatus may be stored in a server device connected via a wired and/or wireless communication network, and the second radiographic imaging apparatus may receive the first radiographic image from the server device.

In operation S13, the second radiographic imaging apparatus obtains attenuation information of the object based on the obtained first radiographic image.

The second radiographic imaging apparatus may determine an equivalent corresponding to the object based on the first radiographic image (operation S14). The equivalent may include a WEO. In detail, the second radiographic imaging apparatus may determine one or more equivalents corresponding to all or part of the object using the attenuation information regarding all or parts of the object of the first radiographic image. When the second radiographic imaging apparatus is the same as the first radiographic imaging apparatus, the second radiographic imaging apparatus may determine an equivalent corresponding to the object based on electrical signals output from the radiographic detector. When a plurality of equivalents is determined for each part of the object, widths of the plurality of equivalents may be different from each other according to characteristics of each part of the object. Consequently, one or more equivalents may be determined, as illustrated in FIG. 10.

According to an exemplary embodiment, the second radiographic imaging apparatus may determine an equivalent by referring to a first lookup table 181 that is first data regarding the relationship between a tube voltage, an attenuation rate, and an equivalent. The first lookup table may be obtained by empirically measuring an equivalent corresponding to the object according to the tube voltage and the attenuation rate.

In operation S15, quality of a second radiographic image to be obtained may be determined after operation S12 is performed. Also, determining the level of quality of the second radiographic image (operation S15) may be performed before or after attenuation information of the object is obtained or may be performed simultaneously with obtaining the attenuation information of the object, in operation S13. In addition, determining the level of quality of the second radiographic image (operation S15) may be performed after an equivalent is determined in operation S14. The quality of the second radiographic image may be selected and determined by the user using an input means, such as a keyboard or a mouse. The quality of the second radiographic image may be selected and determined by the radiographic image obtainer or the CPU of the workstation according to predetermined settings. The quality of the radiographic image may include a noise ratio, resolution, a contrast ratio, or sharpness.

The second radiographic imaging apparatus may obtain one or more tube voltages and tube currents of each equivalent according to the determined image quality (operation S17). As a result, one group of data regarding the tube voltage and the tube current shown in FIG. 12 may be obtained.

According to an exemplary embodiment, the second radiographic imaging apparatus may determine a plurality of sets of tube voltages and tube currents for each equivalent based on the quality of the image by referring to a second lookup table 182 that is second data regarding the relationship between a tube voltage, an equivalent, and a tube current. The second lookup table may be obtained empirically.

If the plurality of sets of tube voltages and tube currents are obtained, expected exposure doses corresponding to the plurality of sets of tube voltage and tube currents may be determined using the obtained tube voltage and tube current (operation S19).

According to an exemplary embodiment, a third lookup table 183 that is third data regarding the relationship between a tube voltage, a tube current, and an expected exposure dose of the radiographic rays may be used to obtain the expected exposure doses. The third lookup table may be obtained by measuring the exposure doses generated according to the tub voltage and the tube current.

The expected exposure dose having a smallest exposure dose may be selected of the obtained expected exposure doses, and a tube voltage and a tube current corresponding to the selected expected exposure dose may be determined (operation S21).

The second radiographic imaging apparatus may display the selected tube voltage and tube current to the user using a display, thereby recommending the selected tube voltage and tube current to the user (operation S22).

The user may determine whether to perform radiographic imaging according to the recommended tube voltage and tube current and may input the result of determination, confirmation, or verification, to the second radiographic imaging apparatus by manipulating an input unit, such as a keyboard or a mouse (operation S23).

If the user determines to perform radiographic imaging according to the recommended tube voltage and tube current, i.e., verifies and confirms the recommended tube voltage and tube current (operation S24), the second radiographic imaging apparatus may apply the applied tube voltage and tube current to the radiographic tube, and the radiographic tube may generate radiographic rays according to the applied tube voltage and tube current. The object is irradiated with the generated radiographic rays, and the radiographic detector receives the radiographic rays transmitted through the object (operation S25).

On the other hand, the user may want to change the tube voltage and tube current, from the recommended tube voltage and tube current (operation S27). If the user wants to change the tube voltage and tube current, the user may input a new tube voltage and a new tube current to be applied to the radiographic tube by manipulating the input unit. The second radiographic imaging apparatus may apply the changed and input tube voltage and tube current to the radiographic tube (operation S28), and the radiographic tube may generate radiographic rays according to the applied tube voltage and tube current. The object may be irradiated with the generated radiographic rays, and the radiographic detector may receive the radiographic rays transmitted through the object (operation S25).

The second radiographic imaging apparatus may generate a second radiographic image using the received radiographic rays (operation S26). The generated second radiographic image may be displayed to the user (operation S31).

When the user determines not to apply the displayed tube voltage and tube current to the radiographic tube and does not input a new tube voltage and a new tube current, the second radiographic imaging apparatus may be driven according to predetermined settings. For example, the second radiographic imaging apparatus may perform a termination process of a radiographic imaging operation (operation S32).

Figure 23:
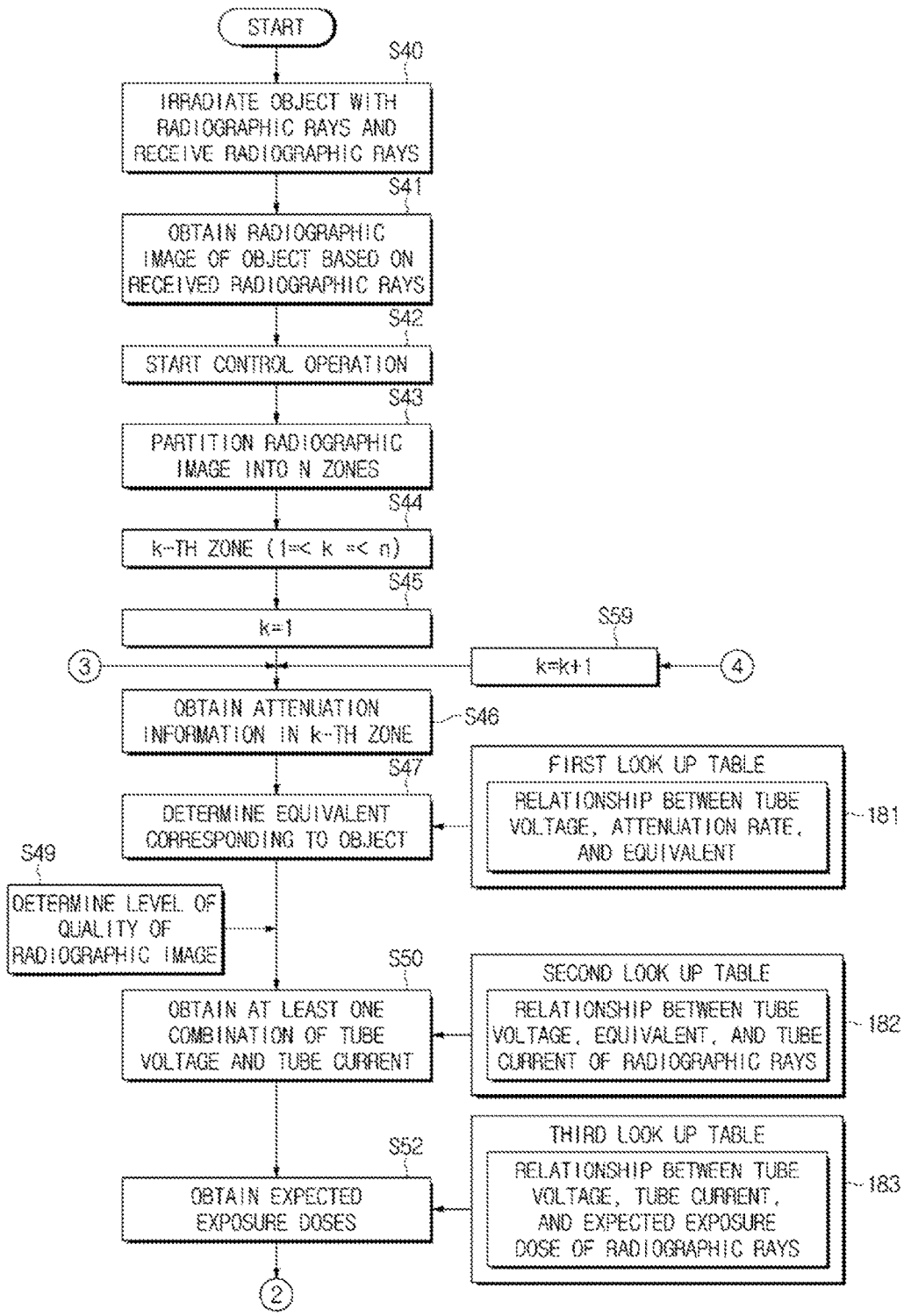
FIGS. 23 and 24 are flowcharts of a method of controlling a radiographic imaging apparatus, according to an exemplary embodiment.
Figure 24:
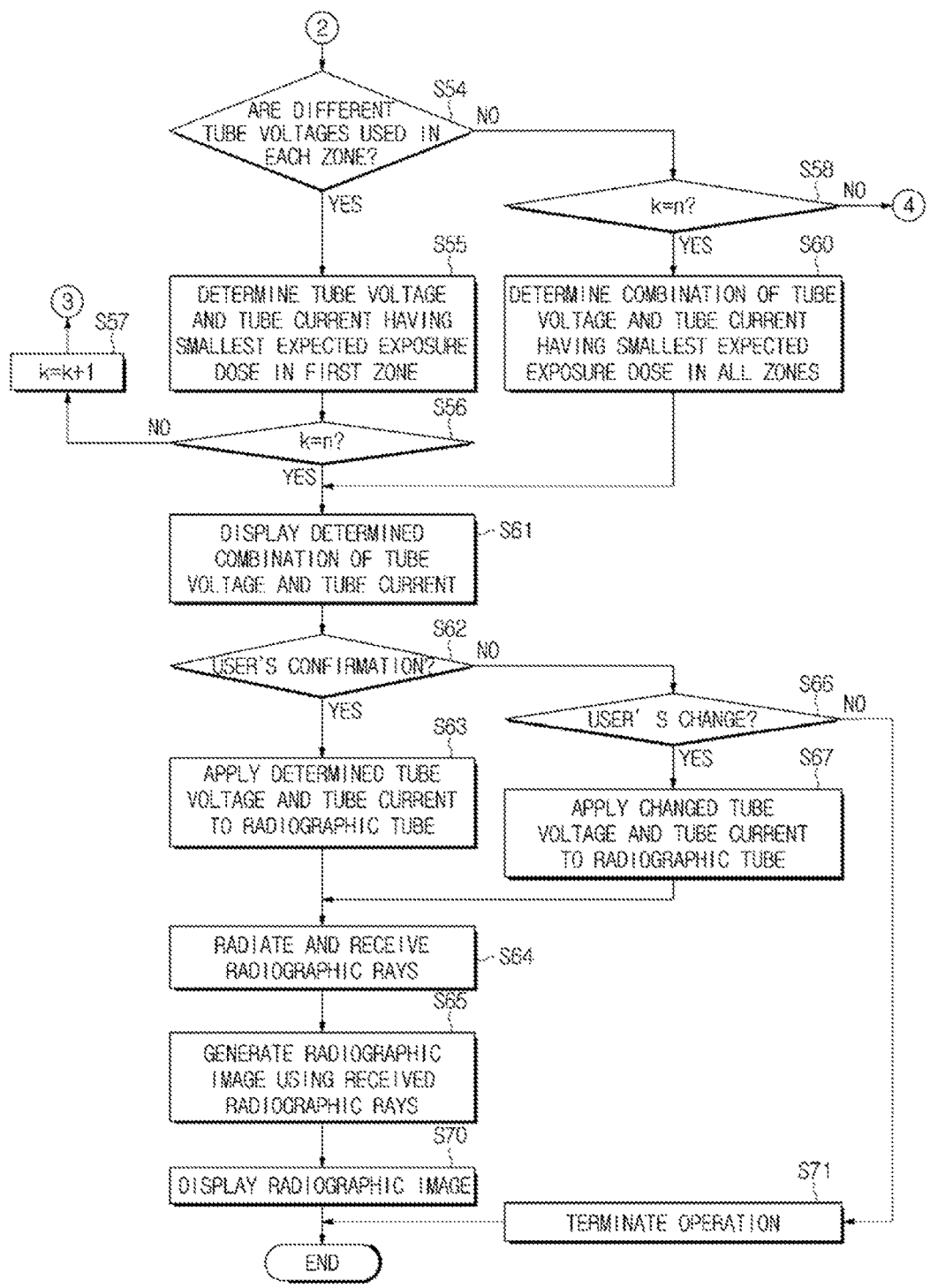

With reference to FIGS. 23 and 24, the first radiographic imaging apparatus may irradiate an object with radiographic rays and may receive the radiographic rays transmitted through the object (operation S40) and may obtain a first radiographic image of the object (operation S41).

If the first radiographic image is obtained, the second radiographic imaging apparatus may start an operation of performing the method of controlling the second radiographic imaging apparatus according to the user's manipulation or predetermined settings (operation S42). As described above with reference to FIGS. 21 and 22, the second radiographic imaging apparatus may be the same as or different from the first radiographic imaging apparatus. Also, the second radiographic imaging apparatus may be the same type as or a different type from that of the first radiographic imaging apparatus.

The second radiographic imaging apparatus may partition the obtained first radiographic image into a plurality of zones, for example, first through n-th zones (operation S43), where n is a natural number that is greater than 1.

The second radiographic imaging apparatus may obtain attenuation information of the object in the first zone (k=1) of the first radiographic image (operations S44, S45, and S46).

Subsequently, the second radiographic imaging apparatus may determine one or more equivalents corresponding to the first zone of the object based on the first radiographic image (operation S47). The one or more equivalents may include WEOs. When a plurality of corresponding equivalents are determined in each part of the first zone, widths of the plurality of corresponding equivalents may be different from each other according to characteristics of each part of the object.

According to an exemplary embodiment, the second radiographic imaging apparatus may determine an equivalent by referring to a first lookup table 181 that is first data regarding the relationship between a tube voltage, an attenuation rate, and an equivalent. As described above, the first lookup table may be obtained by measuring an equivalent corresponding to the object according to the tube voltage and the attenuation rate.

If the equivalent corresponding to the object is determined, one or more tube voltages and tube currents with respect to each equivalent may be obtained (operation S50). The second radiographic imaging apparatus may first determine quality of a second radiographic image.

Determining the quality of the second radiographic image (operation S49) may be performed before or after the attenuation information is obtained in the first zone (operation S46), simultaneously with obtaining the attenuation information in the first zone (operation S46), or after the equivalent is determined (operation S47). The user may determine the quality of the second radiographic image by inputting quality of the second radiographic image by manipulating an input means (operation S49). The radiographic image obtainer or the CPU of the workstation may also determine quality of the second radiographic image according to predetermined settings. The quality of the radiographic image may include a noise ratio, resolution, a contrast ration, or sharpness.

According to an exemplary embodiment, the second radiographic imaging apparatus may determine a plurality of sets of tube voltages and tube currents with respect to each equivalent based on a level of the quality of the image by referring to a second lookup table 182 that is second data regarding the relationship between a tube voltage, an equivalent, and a tube current. The second lookup table may be obtained empirically.

The second radiographic imaging apparatus may determine expected exposure doses using the obtained tube voltages and tube currents (operation S52).

According to an exemplary embodiment, a third lookup table 183 that is third data regarding the relationship between a tube voltage, a tube current, and an expected exposure dose of the radiographic rays may be used to obtain the expected exposure doses. The third lookup table may be obtained by measuring the exposure doses generated according to the tube voltages and tube currents.

In operation S54, it is determined whether the radiographic rays, which are to be radiated onto the object, are to be generated using different or same tube voltages and tube currents in each of the first through n-th zones.

When the radiographic rays are generated using different tube voltages and tube currents in each zone (YES of operation S54), the second radiographic imaging apparatus may select a smallest exposure dose from the obtained expected exposure doses and may determine a tube voltage and tube current to be applied to the radiographic tube to generate the radiographic rays to be radiated in the first zone (k=1) according to the selected smallest exposure dose for the first zone (operation S55).

In operation S56, it is determined whether the tube voltages and tube currents are determined for all of the zones. If it is determined that the tube voltages and tube currents are not determined for all of the zones, the method moves to the next zone k=k+1, in operation S57. In this manner, the second radiographic imaging apparatus may determine n tube voltages and n tube currents to generate the radiographic rays to be radiated in the first through n-th zones by repeatedly performing the operations S46 through S55.

According to an exemplary embodiment, after determining a plurality of sets of tube voltages and tube currents in all zones (first through n-th zones) based on the same image quality, the second radiographic imaging apparatus may determine a tube voltage and a tube current, of which expected exposure dose is smallest, of a plurality of tube voltages and tube currents in each zone. According to another embodiment a plurality of tube voltages and tube currents may be determined based on different image quality in each of the first through n-th zones, and the second radiographic imaging apparatus may determine a tube voltage and a tube current, of which expected exposure dose is smallest of the plurality of tube voltages and tube currents, in each zone. Quality of some of the zones may be the same or different. In this case, the user may select information regarding the quality of the second radiographic image in each zone and may input the selected information using an input means. According to an exemplary embodiment, the user may sequentially input different pieces of information regarding image quality, or may input the information regarding image quality altogether. Image quality in each zone may be determined by the radiographic image obtainer or the CPU of the workstation according to predetermined settings. Through this method, the second radiographic imaging apparatus may determine the tube voltage and tube current in the first through n-th zones in correspondence to the image quality.

If, in operation S56, it is determined that the tube voltages and tube currents are determined for all of the zones, the method proceeds to operation S61, and one or more combinations, i.e., sets, of the determined tube voltages and tube currents may be recommended to the user through the display.

The user may check the recommended tube voltages and tube currents and confirm to radiate radiographic rays according to the recommended tube voltages and tube currents (YES of operation S62). The corresponding tube voltage and tube current may be applied to the radiographic tube in each zone according to the above-described determination (operation S63). In other words, when an image of the first zone is captured, tube voltage and tube current corresponding to the first zone may be applied to the radiographic tube, and when an image of a k-th zone (1<k≤n) is captured, tube voltage and tube current corresponding to the k-th zone (1<k≤n) may be applied to the radiographic tube. Thus, corresponding positions of the first through n-th zones of the object may be irradiated with different radiographic rays caused by applied different tube voltages and tube currents. The radiographic rays may be radiated, transmitted through the object, and received by the radiographic detector (operation S64).

If the user does not confirm the recommended tube voltages and tube currents (NO of operation S62), the user may change tube voltage and tube current to be applied to the radiographic tube (YES of operation S66). The user may change the tube voltage and tube current to be applied, by manipulating an input means, such as a keyboard of the workstation or the radiographic image obtainer.

When the user changes the tube voltage and tube current, the second radiographic imaging apparatus may apply the changed tube voltage and tube current to the radiographic tube (operation S67), and the radiographic tube may generate radiographic rays according to the applied tube voltage. The radiographic rays may be radiated, transmitted through the object, and received by the radiographic detector (operation S64).

The second radiographic imaging apparatus may generate a second radiographic image based on the received radiographic rays (operation S65) and the generated second radiographic image may be displayed (operation S70).

If the user does not confirm the provided tube voltage and tube current (NO of operation S62) and does not change the tube voltage and tube current (NO of operation S66), the second radiographic imaging apparatus may operate according to predetermined settings. For example, if the user does not input instructions of confirmation or change, the second radiographic imaging apparatus determines that the user confirms the provided tube voltage and tube current after a predetermined time elapses and may apply corresponding tube voltage and tube current to the radiographic tube in each zone and may obtain the second radiographic image (operations S63 through S70). The second radiographic imaging apparatus may also terminate an operation relating to radiographic imaging (operation S71).

If, in operation S54, it is determined that the second radiographic imaging apparatus generates radiographic rays using the same tube voltage and tube current in all zones, i.e., in each of the first through n-th zones, the second radiographic imaging apparatus may store a tube voltage, a tube current, and an expected exposure dose obtained in operations S50 and S52.

In operation S58, it is determined whether the tube voltage, tube current, and the expected exposure are determined for all of the zones. If it is determined that the tube voltage, tube current, and the expected exposure are not determined for all of the zones, the method moves to the next zone k=k+1, in operation S59. In this manner, the second radiographic imaging apparatus may determine n tube voltages and n tube currents by repeatedly performing the operations S46 through S52, and the above-described applies here.

If it is determined that the tube voltage, tube current, and the expected exposure are determined for all of the zones, the method proceeds to operation S60. The second radiographic imaging apparatus may determine tube voltage and tube current, of which expected exposure dose is smallest, from the plurality of tube voltages and tube currents obtained in all of the first through n-th zones, and the method may proceed to operation S61. The second radiographic imaging apparatus may first determine tube voltages and tube currents each having smallest expected exposure doses in each zone and then select the tube voltage and tube current having a smallest expected exposure dose of the determined tube voltages and tube currents. An another example, the second radiographic imaging apparatus may select tube voltage and tube current resulting in a smallest expected exposure dose from all of the determined tube voltages and tube currents.

The user may check the recommended tube voltage and tube current and may confirm to radiate radiographic rays according to the recommended tube voltage and tube current (YES of operation S62).

In this case, tube voltage and tube current having the same smallest selected expected exposure dose may be applied to the radiographic tube (operation S63) in each of the first through n-zones. Thus, all zones of the object may be irradiated with the radiographic rays of the same intensity, generated by the same tube voltage and tube current.

As described above, in a radiographic imaging apparatus, a method of controlling the radiographic imaging apparatus, and a CT apparatus according to one or more exemplary embodiments, a user's desired radiographic image can be obtained while minimizing an exposure dose of an object according to the user's desired image quality so that the object, such as the human body, can be prevented from being unnecessarily exposed to a large amount of radiographic rays.

In addition, in the radiographic imaging apparatus, the method of controlling the radiographic imaging apparatus, and the CT apparatus according to the one or more exemplary embodiments, the effect of determining an appropriate tube voltage that is capable of obtaining an image with good quality while minimizing the exposure dose of the object can be achieved.

Furthermore, in the radiographic imaging apparatus, the method of controlling the radiographic imaging apparatus, and the CT apparatus according to the one or more exemplary embodiments, an optimum tube voltage that is capable of obtaining a radiographic image that is suitable for the user with the same or smaller exposure dose can be determined.

Furthermore, in the radiographic imaging apparatus, the method of controlling the radiographic imaging apparatus, and the CT apparatus according to the one or more exemplary embodiments, even when a manipulator of the apparatus does not input information regarding the size or characteristics of the object, the optimum tube voltage can be determined so that the user's convenience of using the radiographic imaging apparatus can be improved.

The foregoing exemplary embodiments and advantages are merely exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A radiographic imaging apparatus comprising:
   a radiographic image obtainer configured to acquire a first radiographic image of an object; and
   a processor configured to obtain attenuation information of the object based on the first radiographic image, determine candidate tube voltages and candidate tube currents based on a quality of a second radiographic image to be obtained, and determine expected exposure doses corresponding to the determined candidate tube voltages and tube currents,
   wherein the processor is configured to determine an equivalent corresponding to the object based on the attenuation information of the object, and determine the candidate tube voltages and tube currents using the determined equivalent.

2. The radiographic imaging apparatus of claim 1, wherein the processor is configured to select a tube voltage and a tube current, from the candidate tube voltages and tube currents, that correspond to a smallest expected exposure dose among the determined expected exposure doses, and recommend the selected tube voltage and tube current to a user, to obtain the second radiographic image.

3. The radiographic imaging apparatus of claim 1, wherein the processor is configured to determine the equivalent corresponding to the object by referring to first data which define a relationship between the candidate tube voltages, attenuation information, and the equivalent.

4. The radiographic imaging apparatus of claim 1, wherein the equivalent comprises a water equivalent object (WEO).

5. The radiographic imaging apparatus of claim 1, wherein the processor is configured to determine the candidate tube voltages and tube currents using second data which define a relationship between the candidate tube voltages, the equivalent, and candidate tube currents.

6. The radiographic imaging apparatus of claim 1, wherein the processor is configured to determine the expected exposure doses corresponding to the candidate tube voltages and tube currents using third data which define a relationship between the candidate tube voltages, candidate tube currents, and expected exposure doses.

7. The radiographic imaging apparatus of claim 1, further comprising an input unit configured to receive a user's input related to the quality of the second radiographic image.

8. The radiographic imaging apparatus of claim 7,
wherein the processor is configured to determine a plurality of voltage-current pairs, each of the plurality of voltage-current pairs corresponding to the user's input related to the quality of the second radiographic image, and
wherein the expected exposure doses correspond to the plurality of voltage-current pairs.

9. The radiographic imaging apparatus of claim 8,
wherein the processor is configured to:
select a voltage-current pair from among the plurality of voltage-current pairs, the selected voltage-current pair corresponding to a smallest expected exposure dose from among the expected exposure doses; and
recommend the selected voltage-current pair to the user to obtain the second radiographic image.

10. The radiographic imaging apparatus of claim 7,
wherein the processor is configured to determine an equivalent corresponding to the object based on the attenuation information of the object, and determine the candidate tube voltages and tube currents using the determined equivalent,
wherein the processor is configured to determine the candidate tube voltages and tube currents using second data which define a relationship between the candidate tube voltages, the equivalent, and candidate tube currents, the second data being determined according to the user's input related to the quality of the second radiographic image.

11. The radiographic imaging apparatus of claim 1, wherein the processor is configured to determine equivalents corresponding to portions of the object.

12. The radiographic imaging apparatus of claim 11, wherein the processor is configured to determine the candidate tube voltages and tube currents based on the quality of the second radiographic image set for each of the equivalents corresponding to the portions of the object, and determine the expected exposure doses corresponding to the candidate tube voltages and tube currents based on the equivalents.

13. The radiographic imaging apparatus of claim 12, wherein the processor is configured to select a tube voltage and a tube current corresponding to a smallest expected exposure dose among the obtained expected exposure doses, and control an irradiation of radiographic rays corresponding to a same tube voltage and a same tube current over an entire object.

14. The radiographic imaging apparatus of claim 12, wherein the processor is configured to select a tube voltage and a tube current corresponding to a smallest expected exposure dose among the obtained expected exposure doses for each of the equivalents corresponding to the portions of the object, and control a generation of radiographic rays corresponding to the selected tube voltage and tube current corresponding to the portions of the object, to irradiate the portions of the object with the radiographic rays of different intensity.

15. A method of controlling a radiographic imaging apparatus, the method comprising:
obtaining a radiographic image of an object;
obtaining attenuation information of the object based on the radiographic image;
determining candidate tube voltages and candidate tube currents based on set quality of an image; and
determining expected exposure doses corresponding to the obtained candidate tube voltages and tube currents,
wherein the determining the candidate tube voltages and tube currents comprises:
determining the attenuation information of the object using the radiographic image; and
determining an equivalent corresponding to the object based on the attenuation information.

16. The method of claim 15, further comprising:
selecting a tube voltage and a tube current that correspond to a smallest expected exposure dose among the obtained expected exposure doses; and
recommending the selected tube voltage and tube current to a user.

17. The method of claim 15, wherein the determining the equivalent comprises:
determining the equivalent corresponding to the object based on the attenuation information of the object by referring to first data which define a relationship between the candidate tube voltages, attenuation information, and equivalent.

18. The method of claim 15, wherein the equivalent comprises a water equivalent object (WEO).

19. The method of claim 15, wherein the determining the candidate tube voltages and tube currents comprises:
determining the candidate tube voltages and tube currents using second data which define a relationship between the candidate tube voltages, equivalent, and candidate tube currents.

20. The method of claim 15, wherein the determining the expected exposure doses comprises:
determining the expected exposure doses corresponding to the candidate tube voltages and tube currents using third data which define a relationship between the candidate tube voltages, candidate tube currents, and the expected exposure doses.

21. The method of claim 15, further comprising receiving information related to the quality of the image from a user.

22. The method of claim 15, further comprising:
determining equivalents corresponding to portions of the object.

23. The method of claim 22, wherein the determining the candidate tube voltages and tube currents comprises determining the candidate tube voltages and tube currents based on the quality of the image set for each of the equivalents corresponding to the portions of the object, and
the determining the expected exposure doses comprises determining the expected exposure doses corresponding to the obtained candidate tube voltages and tube currents based on the equivalents.

24. The method of claim 23, further comprising:
selecting a tube voltage and a tube current corresponding to a smallest expected exposure dose among the obtained expected exposure doses; and
irradiating an entire object with radiographic rays corresponding to a same tube voltage and a same tube current.

25. The method of claim 23, further comprising:
selecting a tube voltage and a tube current corresponding to a smallest expected exposure dose among the obtained expected exposure doses for the equivalents corresponding to the portions of the object; and irradiating the portions of the object with radiographic rays of different intensity, corresponding to the selected tube voltage and tube current corresponding to the portions of the object.

26. A computed tomography (CT) apparatus comprising:
a gantry;
a radiation source which is installed in the gantry and configured to irradiate an object with radiographic rays;
a radiographic detector which is installed in the gantry, and is configured to receive the radiographic rays transmitted through the object and output electrical signals corresponding to the received radiographic rays;
an image processor configured to obtain a first radiographic image based on the output electrical signals; and
a processor configured to obtain attenuation information of the object based on the first radiographic image, determine candidate tube voltages and candidate tube currents based on quality of a second radiographic image to be obtained, and determine expected exposure doses corresponding to the candidate tube voltages and tube currents,
wherein the processor is configured to determine an equivalent corresponding to the object based on the attenuation information of the object, and determine the candidate tube voltages and tube currents using the determined equivalent.

27. The CT apparatus of claim 26, wherein the processor is configured to select a tube voltage and a tube current that correspond to a smallest expected exposure dose from the determined expected exposure doses, and recommend the selected tube voltage and tube current to a user.

* * * * *